(12) United States Patent
Shepard et al.

(10) Patent No.: US 9,080,453 B2
(45) Date of Patent: *Jul. 14, 2015

(54) THERMOGRAPHIC DETECTION OF INTERNAL PASSAGEWAY BLOCKAGES

(71) Applicant: THERMAL WAVE IMAGING, INC., Ferndale, MI (US)

(72) Inventors: Steven M. Shepard, Southfield, MI (US); James R. Lhota, Beverly Hills, MI (US); Tasdiq Ahmed, Windsor (CA); Bharat Bhushan Chaudhry, Troy, MI (US)

(73) Assignee: THERMAL WAVE IMAGING, INC., Ferndale, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/653,168

(22) Filed: Oct. 16, 2012

(65) Prior Publication Data

US 2013/0041614 A1 Feb. 14, 2013

Related U.S. Application Data

(63) Continuation-in-part of application No. 13/050,782, filed on Mar. 17, 2011, now Pat. No. 8,287,183.

(60) Provisional application No. 61/314,848, filed on Mar. 17, 2010.

(51) Int. Cl.
*G01K 1/00* (2006.01)
*F01D 5/18* (2006.01)
(Continued)

(52) U.S. Cl.
CPC ............... *F01D 5/187* (2013.01); *F01D 5/147* (2013.01); *F01D 5/186* (2013.01); *G01J 5/0014* (2013.01);
(Continued)

(58) Field of Classification Search
CPC ......... F01D 5/187; F01D 5/186; F01D 5/147; F01D 21/003; G01J 5/0088; G01J 5/0014; G01J 2005/0077; G01M 99/002; G01N 25/72; G01N 23/04; G01N 29/04; Y02T 50/676; F05D 2230/90; F05D 2260/202
USPC .............................................................. 374/45
See application file for complete search history.

(56) References Cited

U.S. PATENT DOCUMENTS 3,566,669 A 3/1971 Lawrence t al
4,644,162 A 2/1987 Bantel et al.
(Continued)

FOREIGN PATENT DOCUMENTS

CN 1084637 A 3/1994
WO WO-2009079470 A2 6/2009

OTHER PUBLICATIONS

International Search Report and Written Opinion for Application No. PCT/US2011/028886 dated Mar. 17, 2011.
Chinese Office Action for Application No. 201180014141.3 dated May 29, 2014.

*Primary Examiner* — Lisa Caputo
*Assistant Examiner* — Janice M Soto
(74) *Attorney, Agent, or Firm* — Honigman Miller Schwartz and Cohn LLP

(57) ABSTRACT

A method of thermal inspection of a component defining at least one internal passageway at a thermal equilibrium state with its surrounding environment, the method includes: capturing a sequence of thermal indications of a surface of the component, delivering an airflow pulse at the thermal equilibrium state of the at least one internal passageway into the at least one internal passageway, and receiving a temperature response signal as a function of time based on the received thermal indication. The method also includes determining a level of blockage of the at least one internal passageway based on the temperature response signal.

38 Claims, 35 Drawing Sheets

(51) Int. Cl.
*G01J 5/00* (2006.01)
*F01D 5/14* (2006.01)
*G01N 25/72* (2006.01)
*G01M 99/00* (2011.01)
*F01D 21/00* (2006.01)
*G01N 29/04* (2006.01)
*G01N 23/04* (2006.01)

(52) U.S. Cl.
CPC .......... *G01J 5/0088* (2013.01); *G01M 99/002* (2013.01); *G01N 25/72* (2013.01); *F01D 21/003* (2013.01); *F05D 2230/90* (2013.01); *F05D 2260/202* (2013.01); *G01J 2005/0077* (2013.01); *G01N 23/04* (2013.01); *G01N 29/04* (2013.01); *Y02T 50/676* (2013.01)

(56) References Cited

U.S. PATENT DOCUMENTS

| | | | |
|---|---|---|---|
| 5,111,046 | A | 5/1992 | Bantel |
| 6,732,582 | B2 * | 5/2004 | Bunker et al. ............. 73/204.21 |
| 7,075,083 | B2 | 7/2006 | Beyer |
| 7,651,261 | B2 | 1/2010 | Bunker et al. |
| 2005/0008215 | A1 * | 1/2005 | Shepard ...................... 382/141 |
| 2005/0018748 | A1 | 1/2005 | Ringermacher et al. |
| 2006/0039443 | A1 | 2/2006 | Watanabe et al. |
| 2006/0256837 | A1 | 11/2006 | Clifton et al. |
| 2006/0263216 | A1 | 11/2006 | Brummel |
| 2007/0041422 | A1 | 2/2007 | Shepard |
| 2009/0016402 | A1 * | 1/2009 | Bunker et al. ................. 374/43 |
| 2009/0255332 | A1 | 10/2009 | Bunker et al. |
| 2009/0297336 | A1 | 12/2009 | Allen et al. |

* cited by examiner

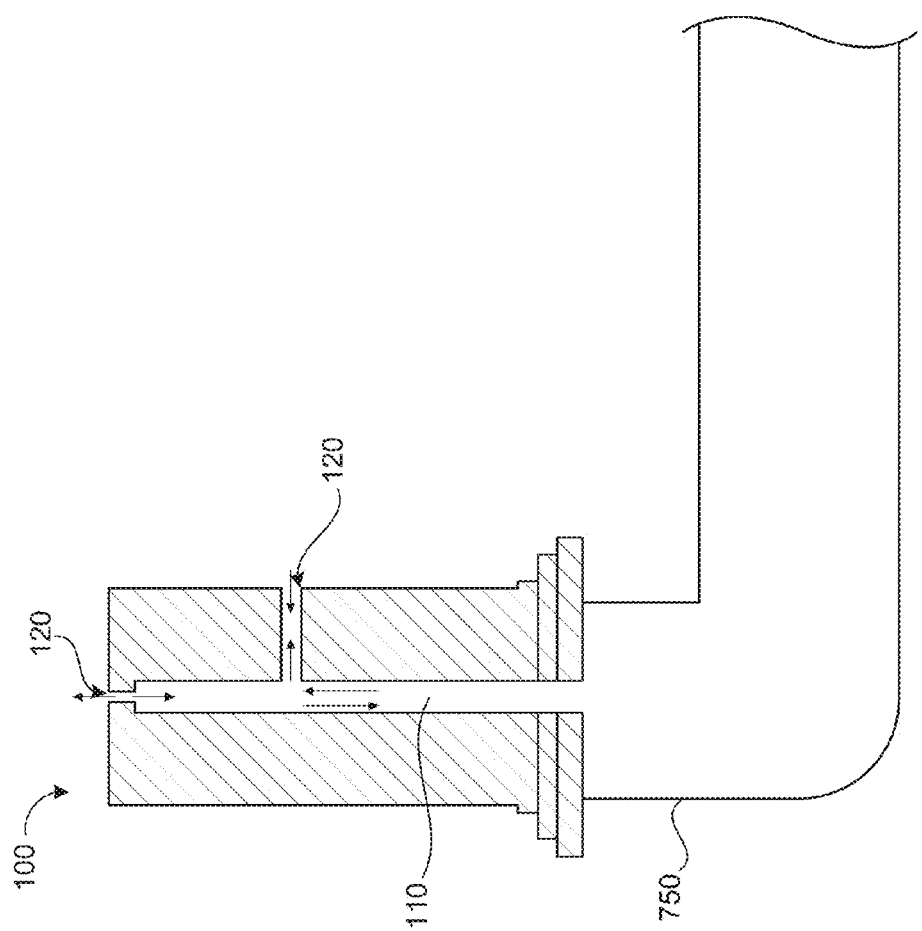

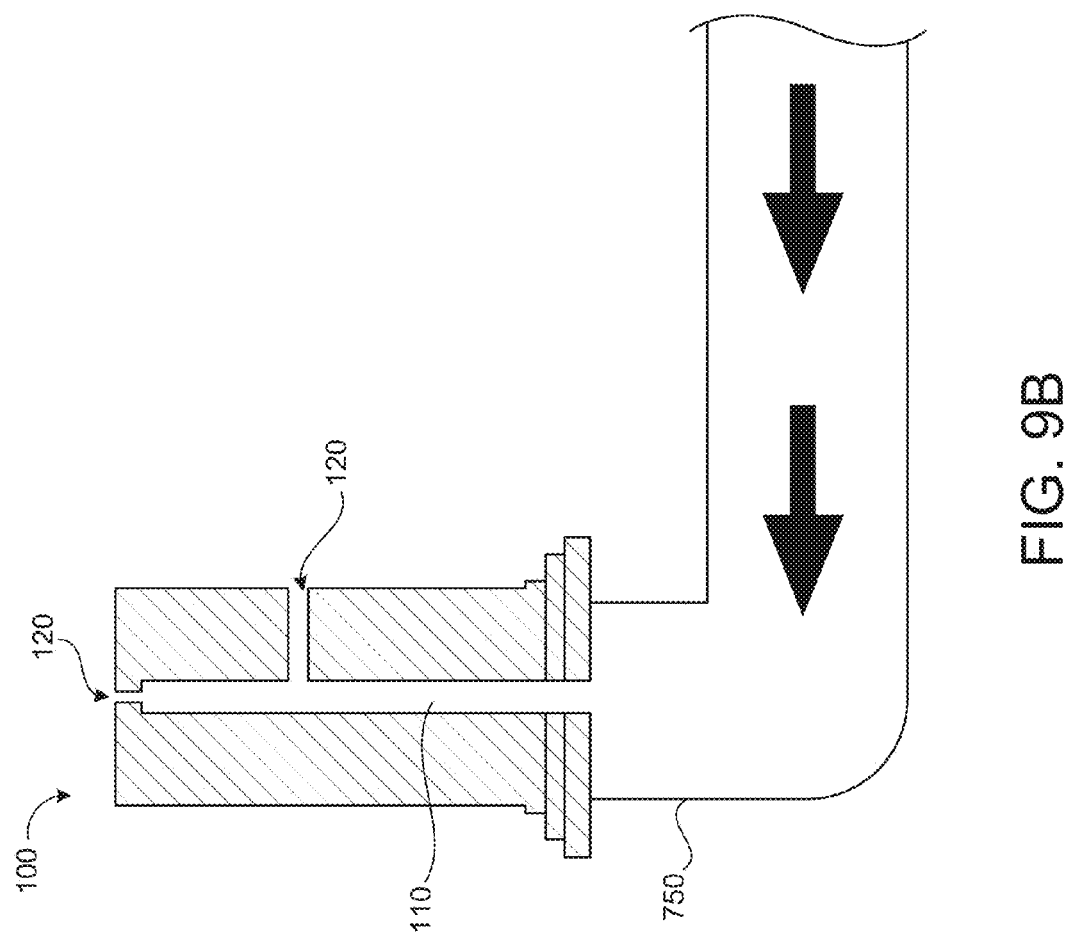

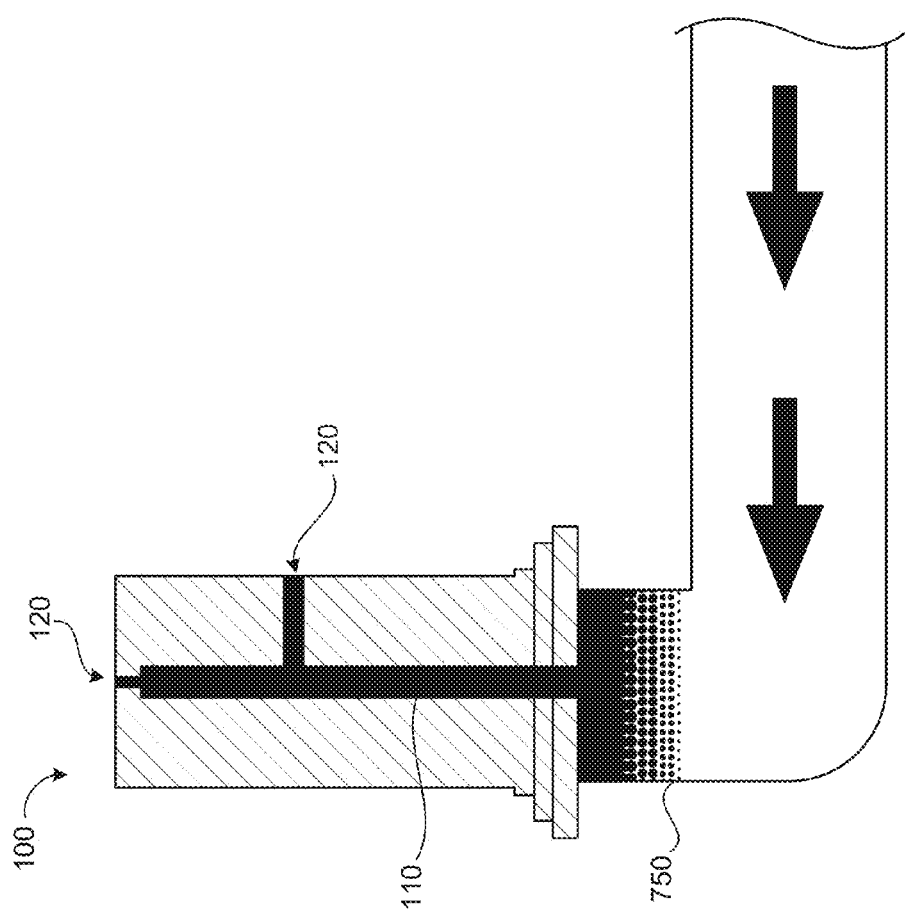

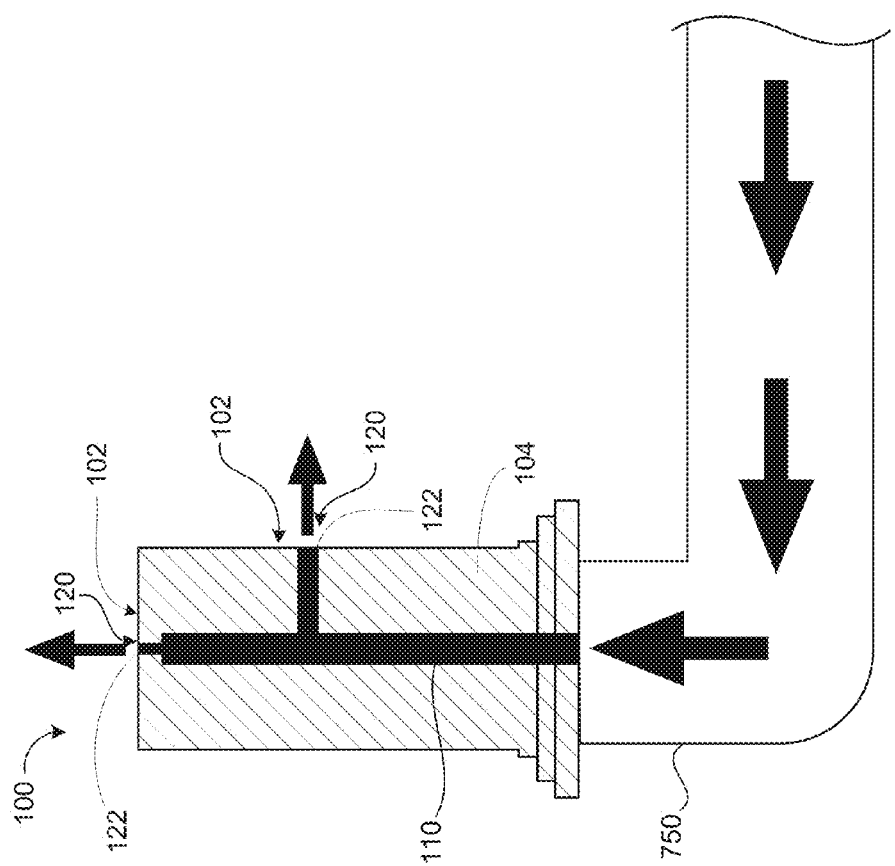

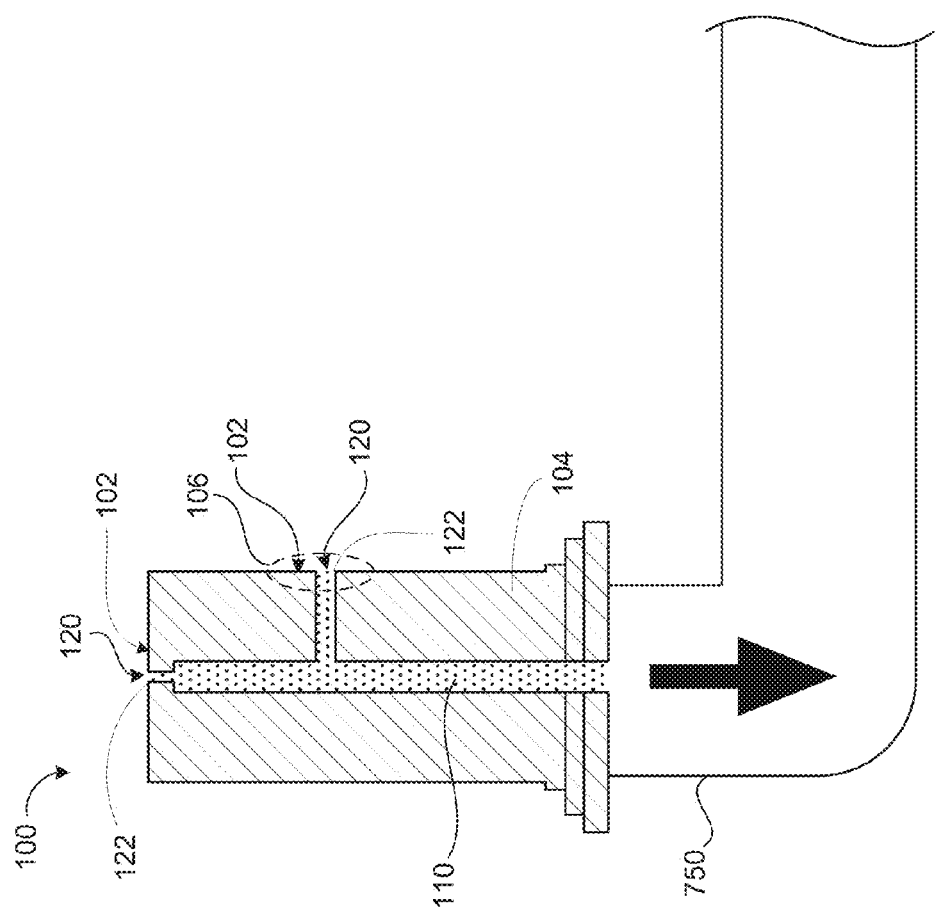

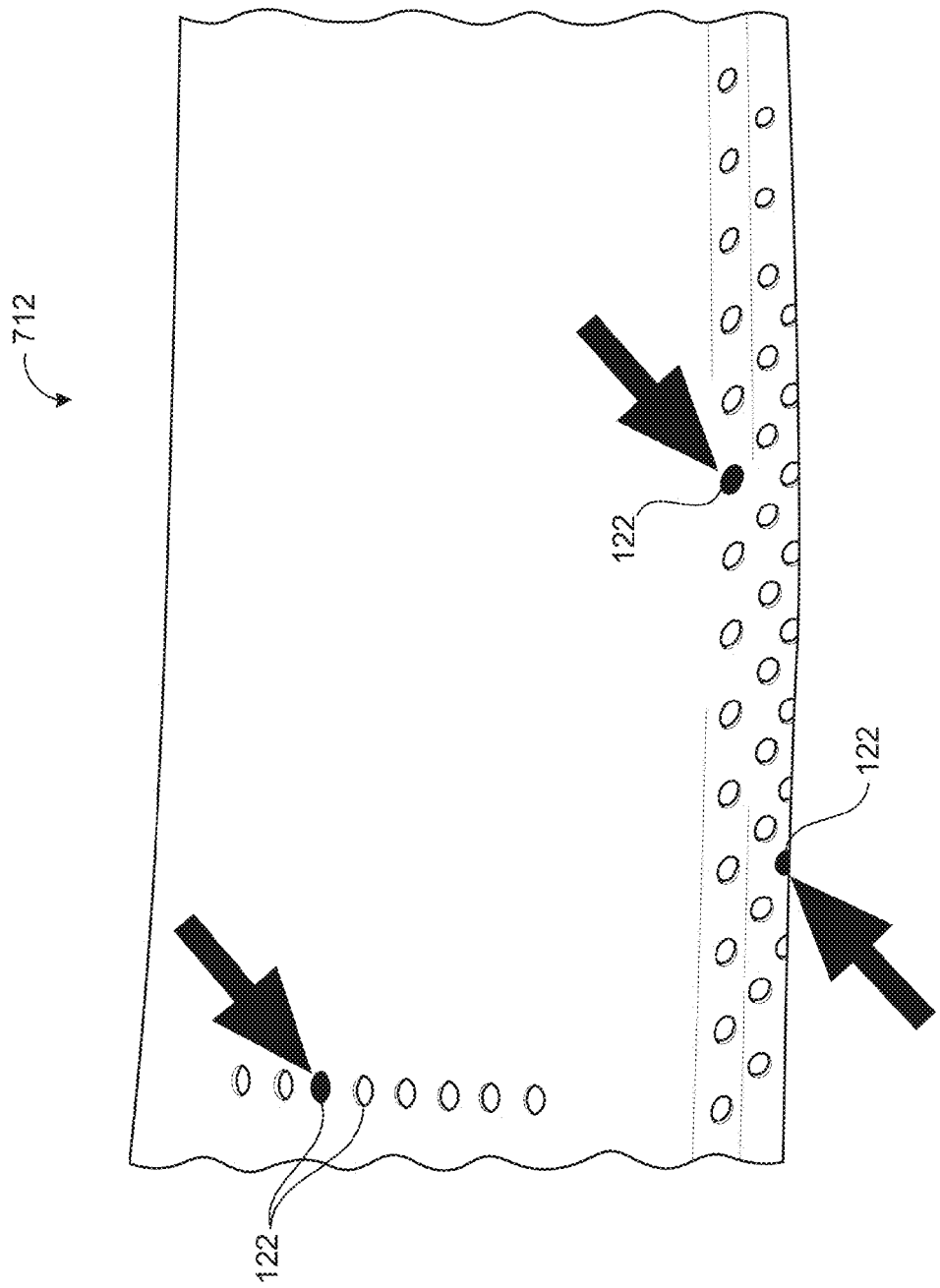

(Reconstructed)

(RAW)

(Reconstructed 1st Derivative)

(Reconstructed 2nd Derivative)

THERMOGRAPHIC DETECTION OF INTERNAL PASSAGEWAY BLOCKAGES

CROSS REFERENCE TO RELATED APPLICATIONS

This U.S. patent application is a continuation of, and claims priority under 35 U.S.C. §120 to, U.S. patent application Ser. No. 13/050,782 filed on Mar. 17, 2011, now U.S. Pat. No. 8,287,183, issued on Oct. 16, 2012, which claims priority under 35 U.S.C. §119(e) to U.S. Provisional Application 61/314,848, filed on Mar. 17, 2010. The disclosures of these prior applications are considered part of the disclosure of this application and are hereby incorporated by reference in their entireties.

TECHNICAL FIELD

This disclosure relates to thermographic detection of internal passageway blockages of an object.

BACKGROUND

For improved thermodynamic efficiency of a gas turbine engine, a high pressure turbine section of the engine may be operated at its highest possible temperature. However, the operating temperature of the turbine increases, so do thermal stresses on turbine airfoil components, such as blades and vanes. These stresses may result in reduced lifetime of the components and potential failure during operation. Modern aircraft turbine engines, as well as ground-based turbines for power generation, have addressed the seemingly divergent requirements for higher operating temperatures and protection and preservation of the turbine airfoils with significant advances in design, materials and manufacturing technologies.

Modern turbines airfoils are generally constructed of metallic superalloys, which provide superior mechanical strength, resistance to creep, oxidation and corrosion, and long fatigue lifetimes at high temperatures compared to conventional metals and alloys. High temperature performance can be further enhanced by a network of internal cooling channels that allow circulation of a cooling fluid (typically air) through the airfoil. Exhaust ducts and holes in the airfoil surface expel air from the internal channels. The holes may be designed to direct a film of cooling fluid along the exterior surface of the airfoil to further enhance cooling.

Various method of using infrared thermography can be used to detect blockages in holes of a component, such as cooling holes of an airfoil. Generally, the methods typically involve pumping a fluid (either hot, cold or alternating hot and cold) through the component and then viewing the resulting infrared image of a surface of the component to determine if the fluid is properly expelled from all holes of the component. In some cases, the gas is chosen to be visible in the infrared spectrum. In other methods, the input and exhaust pressures of the gas are closely monitored with sensors, and deviations in the relationship between these pressures is taken to be an indication of blockage. These methods are generally successful in detecting complete, or near complete blockages, but they are often unable to detect partial blockages.

SUMMARY

In order to operate in high temperature environments that exist in airborne and land based turbines, components such as blades and vanes are typically cooled by a fluid (e.g., air or steam) that flows through an array of internal channels, and is expelled through small exhaust holes on the component surface. Blockage of either a channel or hole during turbine operation results in elevated local temperatures that could cause a critical failure of the component. The present disclosure provides methods for detecting these blockages and other imperfections, defects, and/or features of an analyzed object, such as an airfoil (e.g., a turbine blade or vane).

At present, methods for detecting these blockages are crude and time consuming. For example, a common inspection method requires that an inspector interrogate each hole manually with a wire. Another method involves pumping a fluid through the component, and qualitatively observing the stream flowing from each hole. These methods are imprecise, and often unable to detect partial blockages.

One aspect of the disclosure provides a method of thermal inspection of a component defining at least one internal passageway which attains a thermal equilibrium state with its surrounding environment. The method includes capturing a sequence of thermal indications of a surface of the component, delivering an airflow pulse into the at least one internal passageway wherein said airflow pulse is initially, at least generally, at thermal equilibrium with the internal passageway, and receiving a temperature response signal as a function of time based on the received thermal indications. The method also includes determining a level of blockage of the at least one internal passageway based on the temperature response signal.

In some implementations, the method includes receiving a thermal diffusivity of the component, fitting a mathematical expression to the received temperature response signal, and determining a wall thickness of the component. The method may include, executing thermographic signal reconstruction on a monotonically rising portion of the temperature response signal occurring during a time interval starting at an onset of the air pulse delivery and ending at a time when the temperature response signal attains a maximum temperature, and comparing at least one of a first derivative of the reconstructed temperature response signal with a corresponding first derivative of a reconstructed reference temperature response signal and a second derivative of the reconstructed temperature response signal with a corresponding second derivative of the reconstructed reference temperature response signal to determine if the component meets a specification.

In some examples, delivering the airflow pulse includes expelling a film of air across a surface of the component. Additionally or alternatively, the method may include determining a shape of the air film based on at least one a representation, and comparing the determined air film shape to a reference shape to determine whether the exit hole meets a specification.

The method may include identifying a monotonically rising portion of the temperature response signal occurring during a time interval starting at an onset of the air pulse delivery and ending at a time when the temperature response signal attains a maximum temperature, and identifying a monotonically falling portion of the temperature response signal occurring during a time interval starting at cessation of the air pulse delivery and ending at a time when the temperature response signal reaches a minimum temperature. In some examples, the method includes determining a first derivative of the temperature response signal, and determining the level of blockage of the at least one internal passageway based on the first derivative of the temperature response signal.

In some examples, the method includes capturing a first sequence of thermal indications before the component has been subjected to use as its intended purpose, and capturing a second sequence of thermal indications after the component has been subjected to use as its intended purpose. Additionally or alternatively, the method may include comparing the first and second sequence of thermal indications and determining a level of blockage of the at least one internal passageway based on the compared indications.

Another aspect of the invention provides a method of thermal inspection of a component that defines at least one internal passageway. The method includes receiving a sequence of thermal indications of a surface of the component, delivering a fluid pulse into the at least one internal passageway, compressively heating the at least one internal passageway by way of delivering the fluid pulse, and receiving a temperature response signal as a function of time based on the received indications caused by the compressive heating. In some examples, the duration of compressively heating the at least one internal passageway is on the order of tens of milliseconds.

In some examples, the method includes identifying a location of the at least one internal passageway based on the sequence of thermal indications, and applying a line segment along each identified passageway. The method may include determining a first derivative of the temperature response signal at a particular time for every point along the line segment with one or more reference signals to determine if the component meets a specification. The method may further include verifying one of placement, size, arrangement, and level of blockage of the internal passageway by way of a time history of temperature change of the component.

The method, in some implementations, includes capturing a first sequence of thermal indications before the component is subjected to use, capturing a second sequence of thermal indications after the component is subjected to use, and comparing the first and second set of thermal indications for verifying one of placement, size, arrangement, and level of blockage of the internal passageway.

Another aspect of the invention provide a method of thermal inspection of a component defining at least one internal passageway having static fluid present therein at a thermal equilibrium state with its surrounding environment. The method includes receiving a continuous sequence of thermal images of at least an exit hole defined by the at least one internal passageway at a surface of the component, delivering an airflow pulse into the at least one internal passageway for expelling the static fluid, the airflow pulse disrupting the thermal equilibrium state of the at least one internal passageway by way of compressive heating, and receiving a temperature response signal as a function of time based on the received thermal images of the pressurized airflow pulse. The method also includes delivering a continuous steady flow of pressurized air into the at least one internal passageway. The method may further include receiving a first sequence of thermal images before the component is subjected to use, receiving a second sequence of thermal images after the component is subjected to use, and comparing the first and second sequences of thermal images for verifying one of the placement, size, arrangement, and level of blockage of the internal passageway.

In some implementations, the method includes executing thermographic signal reconstruction on a monotonically rising portion of the temperature response signal occurring during a time interval starting at an onset of the air pulse delivery and ending at a time when the temperature response signal attains a maximum temperature, and comparing at least one of a first derivative of the reconstructed temperature response signal with a corresponding first derivative of a reconstructed reference temperature response signal and a second derivative of the reconstructed temperature response signal with a corresponding second derivative of the reconstructed reference temperature response signal to determine if the component meets a specification.

Delivering an airflow pulse may include expelling a film of air across a surface of the component, determining a shape of the air film based on at least one a representation, and comparing the determined air film shape to a reference shape to determine whether the exit hole meets a specification. In some examples, the method further includes identifying a monotonically rising portion of the temperature response signal occurring during a time interval starting at an onset of the air pulse delivery and ending at a time when the temperature response signal attains a maximum temperature, and identifying a monotonically falling portion of the temperature response signal occurring during a time interval starting at cessation of the air pulse delivery and ending at a time when the temperature response signal reaches a minimum temperature.

Another aspect of the disclosure provides a testing system. The testing system includes a pressurized air source configured to direct fluid to a component having at least one internal passageway at a thermal equilibrium state with its surrounding environment. The system also includes a thermal indicator arranged to capture a status of the component, and a computing device in communication with the indicator. The computing device receives a sequence of thermal indications of at least an exit hole defined by the at least one internal passageway at a surface of the component, causes the air source to deliver a pressurized airflow pulse at the thermal equilibrium state of the at least one internal passageway into the at least one internal passageway of the component, and determines a temperature response signal as a function of time based on the received indications. The computing device determines a level of blockage of the at least one internal passageway.

In some implementations, the computing device captures a first sequence of thermal indications before the component is subjected to use and a second sequence of thermal indications after the component is subjected to use, and compares the first and second sequence of thermal indications for verifying one of the placement, size, arrangement, and level of blockage of the internal passageway. The computing device may determine a first derivative of the temperature response signal and compare the first derivative of the temperature response signal with a first derivative of the temperature response signal of the component determined before exposure of the component to its intended use. The computing device may identify peaks of the first derivative of the temperature response signal to determine the onset time period and the shut-off time period.

Another aspect of the disclosure provides a method of thermal inspection of a component during a portion of its lifetime, the lifetime having an operational phase and a testing phase, wherein during its operational phase the component is being used for its intended purpose. The component defines at least one internal passageway. The method includes moving the component from the operational phase to a testing phase, capturing a sequence of thermal indications of a surface of the component, and delivering an airflow pulse into the at least one internal passageway at an initial time $t_0$. The method also includes receiving a temperature response signal as a function of time based on the received thermal indication, fitting a first mathematical expression to the received temperature response signal for a duration of time $t_{d1}$ wherein $t_0 < t_{d1} < t_1$, and fitting a second mathematical expression to the received temperature response signal for a second duration of time $t_{d2}$ wherein $t_1 < t_{d2} < t_c$ where $t_c$ indicates a shutoff time of the airflow pulse. The method also includes returning the component from the testing phase to the operational phase, and comparing the first and second mathematical expressions with another first and second mathematical expressions fitted before moving the component from the operational phase to the testing phase.

In some examples, the method includes fitting a third mathematical expression to the received temperature response signal for a third duration of time $t_3$ wherein $t_c < t_3 < t_f$ and $t_f$ is a final time of the thermal inspection. The method may include comparing the third mathematical expression with another third mathematical expression fitted before moving the component from the operational phase to the testing phase. The first mathematical expression may be different from the second mathematical expression. In some examples, the first mathematical expression is:

$$T_{temp-ON} = \frac{1}{T}\left(1 + 2\sum_{n=1}^{\infty} e^{\alpha n^2 \pi^2 t/L^2} \cos(n\pi)\right)$$

wherein $T_{emp-ON}$ is a temperature of the external surface of the component, T is the thickness of the component, and $\alpha$ is the thermal diffusivity of the component. Additionally or alternatively, the second mathematical expression is:

$$E(t) = Ae^{-B(t-t0))} + C$$

wherein A, B and C are calculated using a least square fit.

Another aspect of the disclosure provides a thermographic testing system for inspecting a component during a portion of its lifetime, the lifetime having an operational phase and a testing phase, wherein during its operational phase the component is being used for its intended purpose, during the testing phase. The testing system includes an air source configured to direct fluid to a component having at least one internal passageway, a thermal indicator arranged to capture a status of the component, and a computing device in communication with the indicator. The computing device captures a sequence of thermal indications of a surface of the component, delivers an airflow pulse into the at least one internal passageway at an initial time $t_0$, receives a temperature response signal as a function of time based on the received thermal indication. The computing device also includes fitting a first mathematical expression to the received temperature response signal for a duration of time $t_{d1}$ wherein $t_0 < t_{d1} < t_1$, and fitting a second mathematical expression to the received temperature response signal for a second duration of time $t_{d2}$ wherein $t_1 < t_{d2} < t_c$ where $t_c$ indicates a shutoff time of the airflow pulse. The computing device also includes returning the component from the testing phase to the operational phase; and comparing the first and second mathematical expressions with another first and second mathematical expressions fitted before moving the component from the operational phase to the testing phase.

In some implementation, the computing device fits a third mathematical expression to the received temperature response signal for a third duration of time $t_3$ wherein $t_c < t_3 < t_f$ and $t_f$ is a final time of the thermal inspection. Additionally or alternatively the computing device may compare the third mathematical expression with another third mathematical expression fitted before moving the component from the operational phase to the testing phase. The first mathematical expression may be different than the second mathematical expression. The first mathematical expression may be:

$$T_{temp-ON} = \frac{1}{T}\left(1 + 2\sum_{n=1}^{\infty} e^{\alpha n^2 \pi^2 t/L^2} \cos(n\pi)\right)$$

wherein $T_{emp-ON}$ is a temperature of the external surface of the component, T is the thickness of the component, and $\alpha$ is the thermal diffusivity of the component. In some examples, the second mathematical expression is:

$$E(t) = Ae^{-B(t-t0))} + C$$

wherein A, B, and C are calculated using a least square fit.

The details of one or more implementations of the disclosure are set forth in the accompanying drawings and the description below. Other aspects, features, and advantages will be apparent from the description and drawings, and from the claims

DESCRIPTION OF DRAWINGS

FIG. 9A is a schematic view of an exemplary turbine airfoil in equilibrium with its surrounding environment.

FIG. 9B is a schematic view of the turbine airfoil shown in FIG. 9A initially receiving a pressurized airflow.

FIG. 9C is a schematic view of the turbine airfoil experiencing internal heating due to a rapid compression of previously static air in internal passageways of the turbine airfoil.

FIG. 9D is a schematic view of the compressed air within the turbine airfoil shown in FIG. 9C escaping through exit passageways defined by the airfoil.

FIG. 9E is a schematic view of air expanding in the turbine airfoil shown in FIG. 9D after cessation of delivery of the pressurized air.

FIG. 10D is a side view of an image of an exemplary turbine airfoil having marked identified blocked holes.

Like reference symbols in the various drawings indicate like elements.

DETAILED DESCRIPTION

Component manufacturing may entail many steps, some of which may include quality inspections. Although the present disclosure describes various methods and apparati for turbine airfoil manufacturing and inspection, these methods and apparati may be used on other types of components as well, and in subsequent inspections after the component has been in service.

Figure 1:
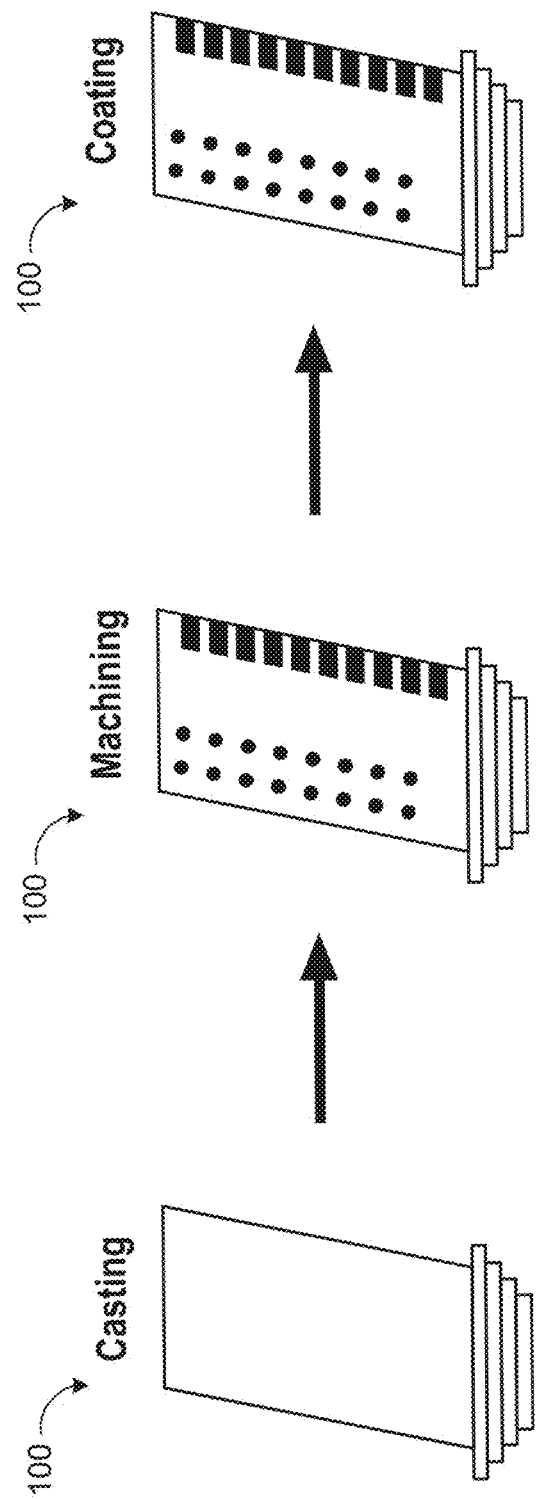
FIG. 1 is a schematic view of a turbine airfoil manufacturing process.
Figure 2:
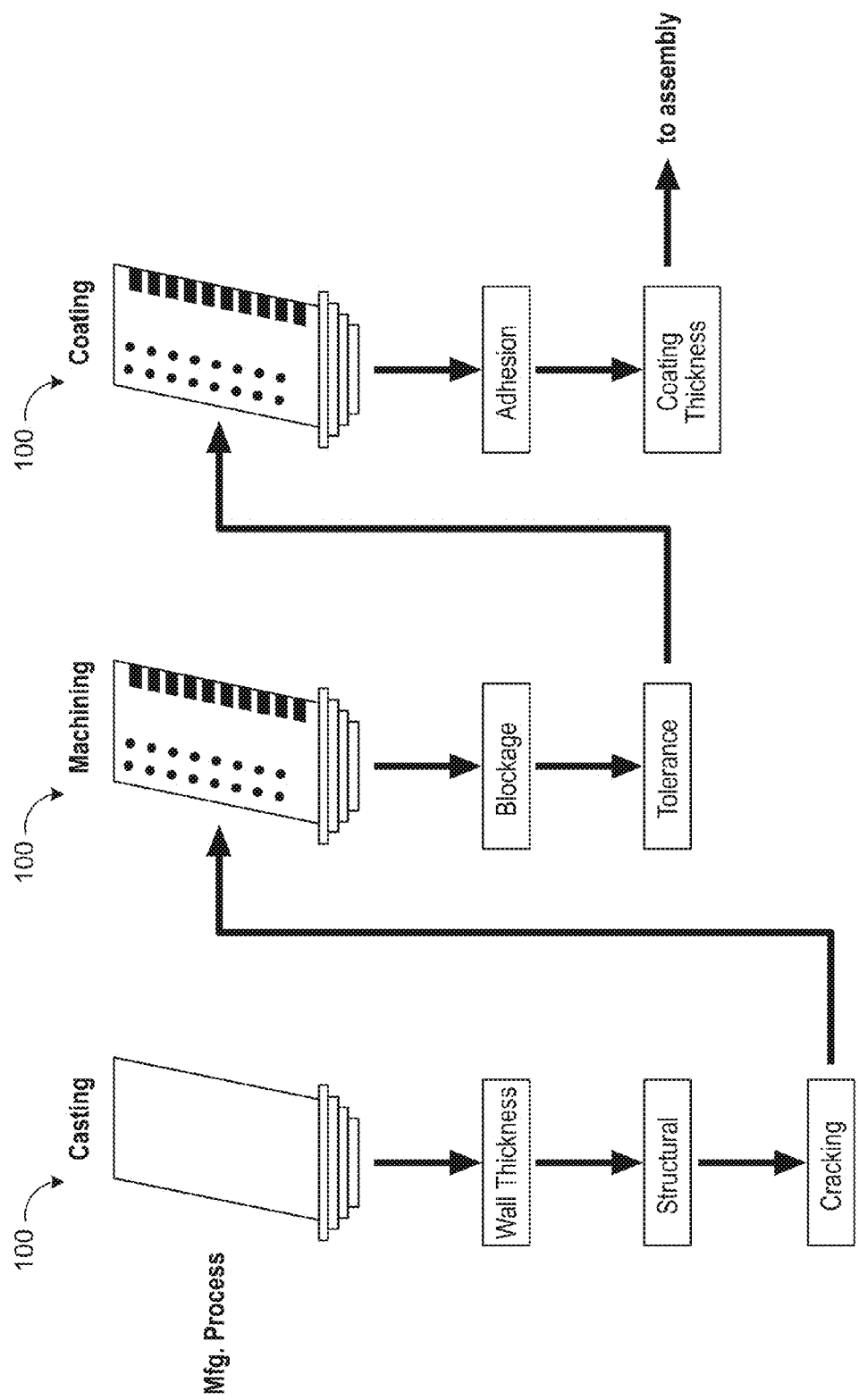
FIGS. 2 and 3 are schematic views of quality assurance testing procedures for a turbine airfoil manufacturing process.
Figure 3:
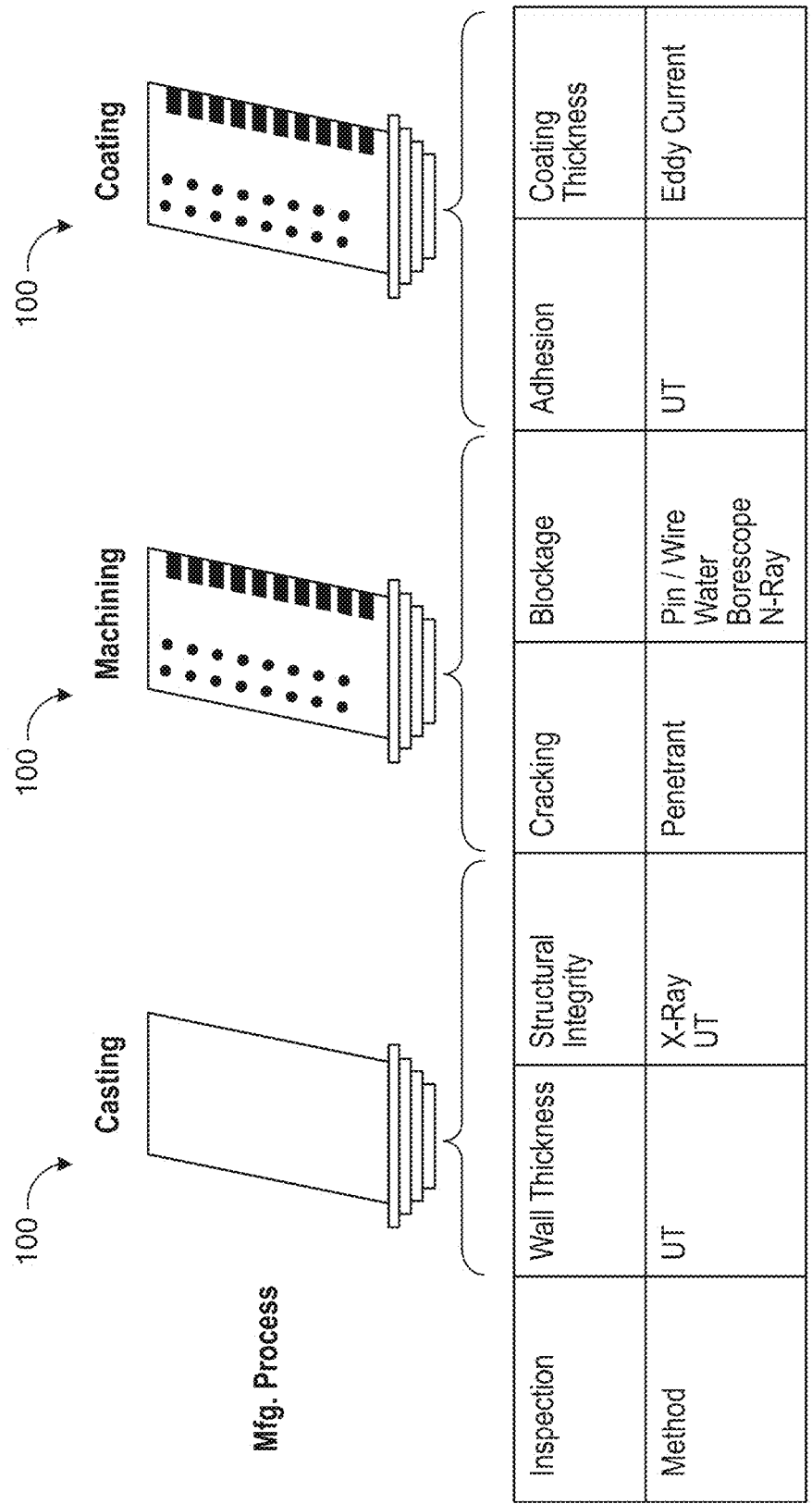

Referring to FIGS. 1-3, the manufacture of a turbine airfoil 100 may include several steps, such as a casting, machining, and coating the airfoil 100. The casting process may include pouring a molten superalloy into a mold cavity having ceramic cores that define an internal cooling channel network. After casting the airfoil 100, the ceramic cores can be removed by a chemical leaching process. Multiple inspections can be performed at each manufacturing step or operation. For example, after casting the airfoil 100, a quality inspection may include measuring structural features of the airfoil 100, such as an overall size and/or wall thicknesses, proper formation and placement of internal channels and structures, and checking for cracks or defects. The machining operation may entail forming various features into the airfoil 100, such as cooling channels, passageways, and/or holes. After the machining operation, the airfoil 100 can be inspected for feature size tolerances and/or at least partial blockage of the channels, passageways, or holes. During the coating operation, a thermal barrier coating (TBC) may be applied to the airfoil to enhance performance. After the coating operation, the airfoil 100 may be inspected for adhesion of the coating (e.g., de-lamination), a coating thickness, and/or at least partial blockage of the channels, vanes, or holes.

A number of problems that affect airfoil operational performance may occur during the manufacturing process. For example, residue or debris from the ceramic cores used in casting may remain after the leaching process and create blockages in internal cooling channels. Moreover, the ceramic cores may shift position during the casting process, so that the cast airfoil 100 does not conform to a specification. Other problems may include incomplete machining of cooling holes that results in complete or partial blockage of the hole, compromising cooling performance. Holes may be improperly positioned or drilled at angles outside of the specification. In laser machining, the diameter of a hole may not be consistent through an airfoil wall. Moreover, debris created during the machining process may enter internal cooling passages and create blockages. The coating process may obstruct cooling holes or create debris that enters the internal cooling passageways and creates blockages.

Figure 5:
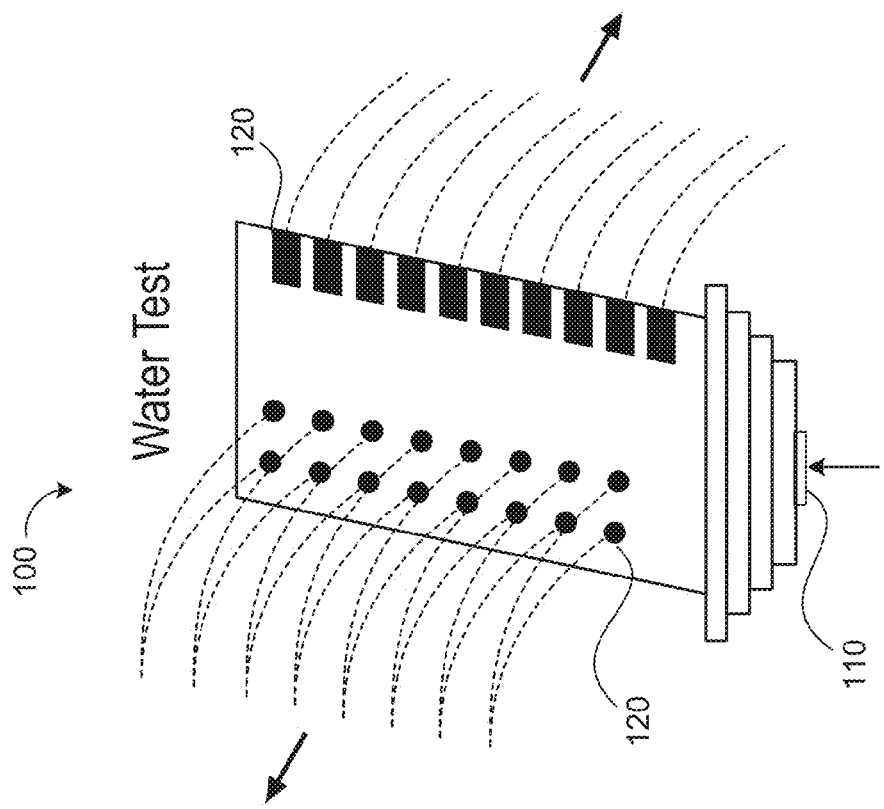
FIG. 5 is a schematic view of a water test for checking blockage of a passageway of an exemplary turbine airfoil.
Figure 4:
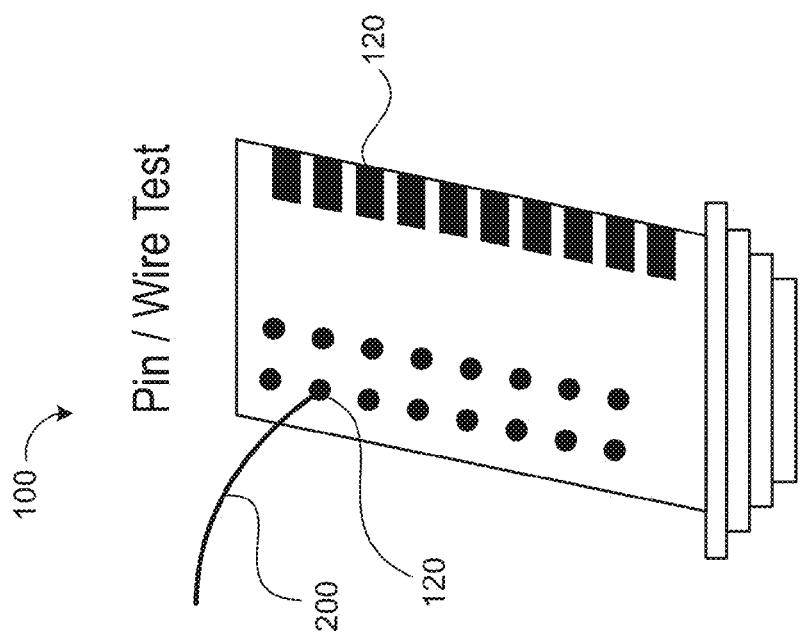
FIG. 4 is a schematic view of a pin/wire test for checking blockage of a passageway of an exemplary turbine airfoil.

Inspections at each manufacturing operation may include different inspection methods and equipment for analyzing various aspects of the airfoil 100 or for determining various quality metrics. These inspection methods may include ultrasonic testing (UT), X-ray, neutron radiography (N-ray), liquid penetrant inspections, flowing of water therethrough, borescope, pin/wire hole inspection, eddy current analysis, and infrared thermography. For example, after the casting operation, infrared thermography, ultrasonic testing, and/or X-ray testing can be used to determine the structural integrity (e.g., features sizes, wall thicknesses, etc.) of the airfoil 100. After the machining operation, infrared thermography, liquid penetrant inspections, flowing of water therethrough, borescope, and/or pin/wire hole inspections can be used to determine if the airfoil 100 has any cracks or blocked passageways. FIG. 4 illustrates manual insertion of a wire 200 into an exit passageway 120 of the airfoil 100 for determining whether the exit passageway 120 is blocked. The manual wire inspection can be time consuming for large quantities of exit passageways 120, subjective for each operator, and cannot detect partial blockages in complex paths of internal passageways. FIG. 5 illustrates flowing water into an inlet passageway 110 of the airfoil 110, which is in fluid communication with one or more exit passageways 120. A blocked cooling passageway can be detected by a relative flow rate out of each exit passageway 120; however, the method can be subjective and small blockages can be difficult to detect. After the coating operation, infrared thermography and/or ultrasonic testing (UT) can be used to determine an adhesion quality (e.g., by identifying any areas of de-lamination). Moreover, eddy current testing may be used to determine a coating thickness on the airfoil 100.

Figure 6:
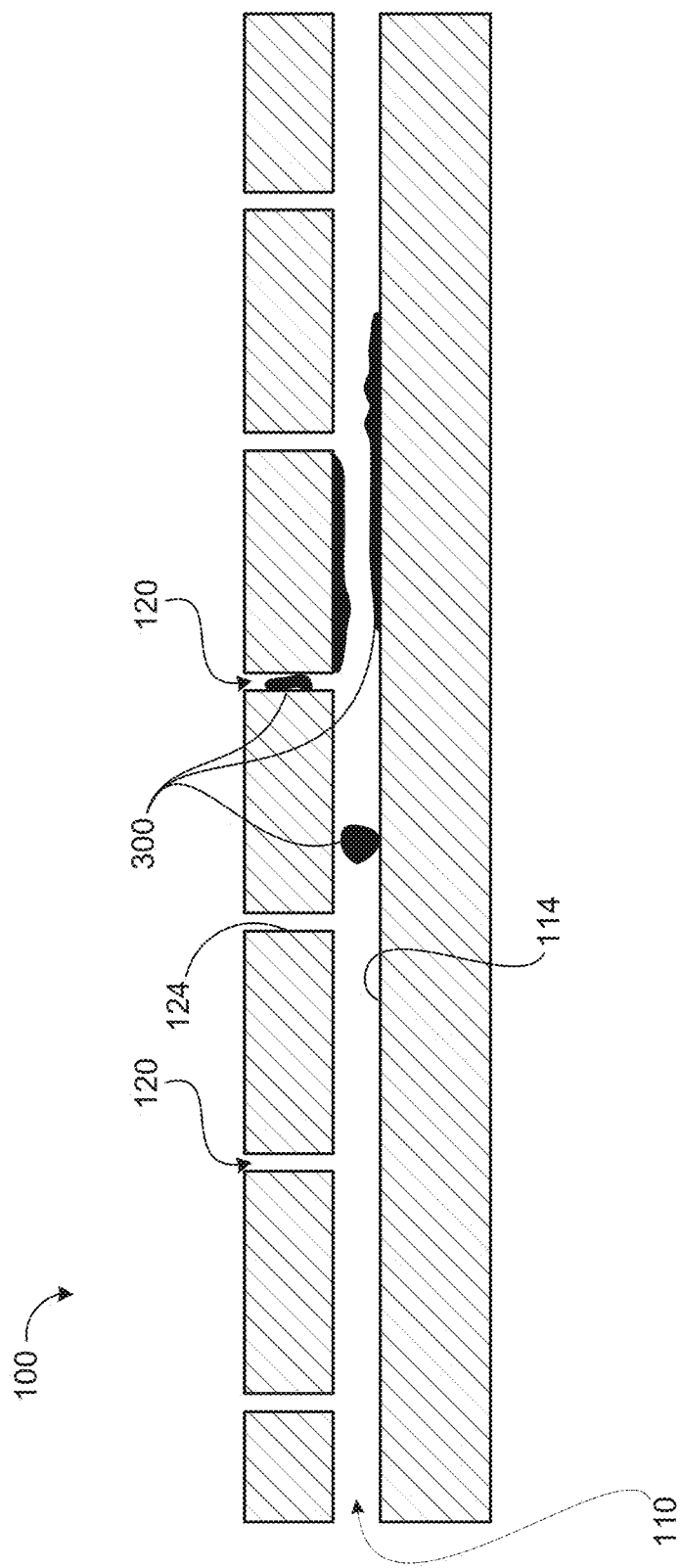
FIG. 6 is a section view of an exemplary turbine airfoil wall.

FIG. 6 provides a section view of a portion of an exemplary airfoil 100 having an inlet passageway 110 in fluid communication with exit passageways 120. In the example shown, debris 300 can accumulate on walls of the passageways 110, 120, deceasing a cross-sectional flow area, and in some instances, entirely blocking one or more of the passageways 110, 120. The debris 300 may enter the airfoil 100 from any number of sources, such as machining debris, coating material, foreign objects in coolant flowed therethrough, residual core from the casting process, etc. A method of infrared thermography may be used to inspect the airfoil 100 after each manufacturing step as well as during maintenance of the airfoil while in commercial operation.

A method of infrared thermographic inspection can be used to detect blockages in airfoil cooling holes and residual core debris in internal channels as well as confirmation of proper operation of film cooling over an airfoil surface. Film cooling may occur when internal passageways and exit holes are unblocked and exit holes are oriented to expel air over the airfoil surface. The inspection method does not require extensive airfoil preparation before testing or air temperature conditioning during inspection. Moreover, the inspection method allows inspection of the entire air foil 100 in a period of a few seconds. While aspects of the inspection method can be enhanced by using a reference airfoil having verified unblocked internal passageways and exit holes, the inspection method can identify blockages using other a priori information and/or based on simple indicators in resultant data.

Figure 7:
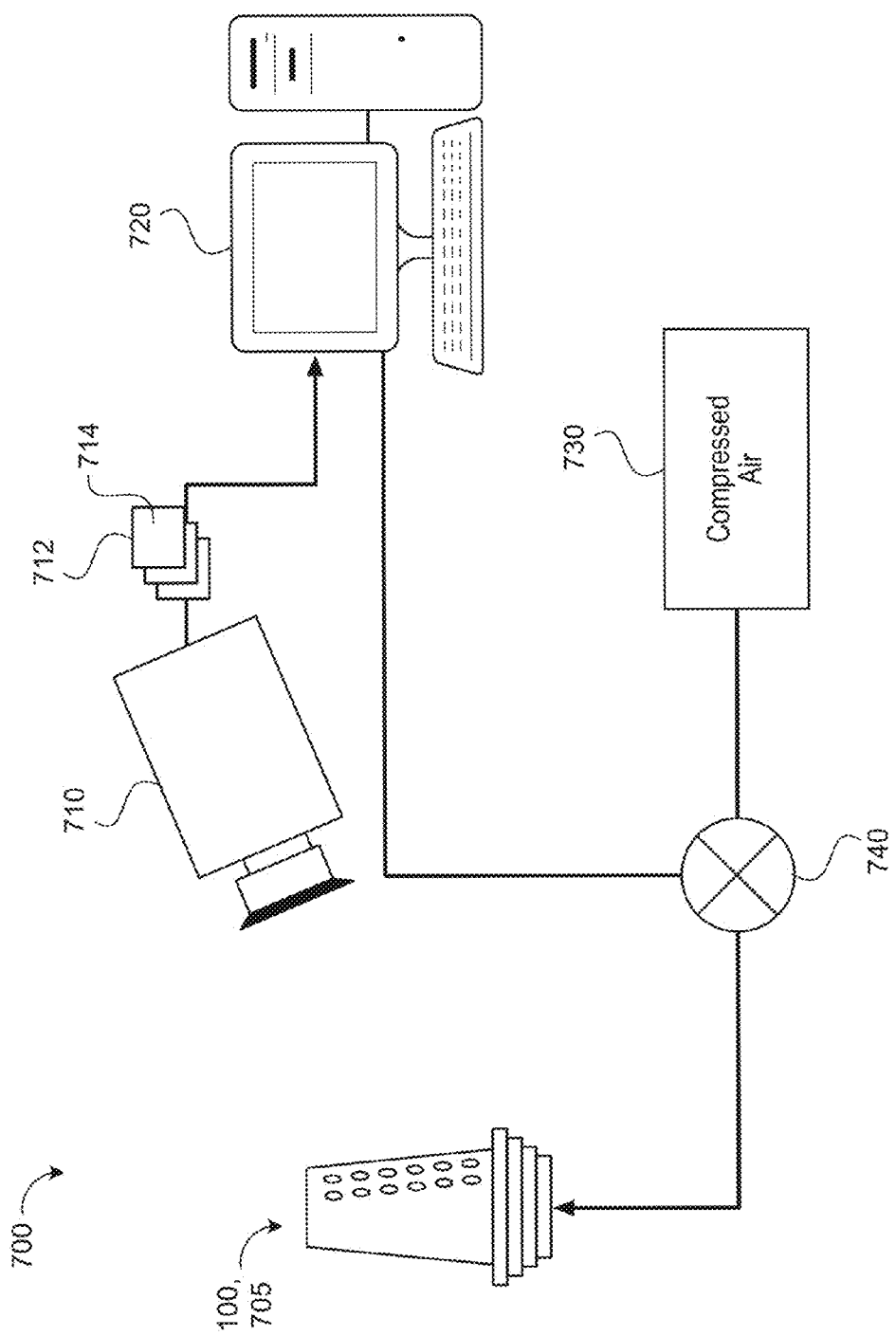
FIG. 7 is a schematic view of thermographic testing system for detecting features and/or blocked internal passageways of an object.

Referring to FIG. 7, in some implementations, a system 700 for thermographically testing a component 705 having at least one internal passageway, such as the turbine airfoil 100, includes an infrared camera 710, a computing device 720 (e.g., a device having a processor and/or memory) in communication with the infrared camera 710, and a compressed air source 730 configured to receive fluid communication with the component. A valve 740 in communication with the computing device 720 may control a flow of air (e.g., at room temperature or any temperature) from the compressed air source 730 to the component 705. For example, the computing device 720 can control a pressure level of the air flow delivery, a pulse duration, pulse sequence, etc. by controlling the valve 740. The infrared camera 710 is arranged to monitor at least a portion of the component 705. In the example shown, the infrared camera 710 is arranged to view the entire airfoil 100 as the component 705 from one perspective. Mirrors can be used to view multiple sides of the component 705. The infrared camera 710 provides at least one thermal image 712 comprised of pixels 714 (e.g., a sequence of thermal images 712). The computing device 720 receives imaging signals from the infrared camera 710 and may determine a temperature response signal (temperature as a function of time) for each pixel 714. For example, the computing device 720 can have digital image acquisition or analog frame-grabbing capabilities to convert signals or data received from the infrared camera 710 to a format that can be analyzed and mathematically manipulated by the computing device 720. The computing device 720 does not necessarily need to be separate from the camera 710 and that the functions in the computing device 720 can be incorporated into the camera 710 itself as, for example, an on-board integrated circuit. Moreover, the computing device 720 may include an optional acquisition module for generating a complete mosaic image of an imaged sample when the camera 710 obtains multiple spatially different images 712, particularly when the sample is too large to fit in a single image frame.

Figure 8A:
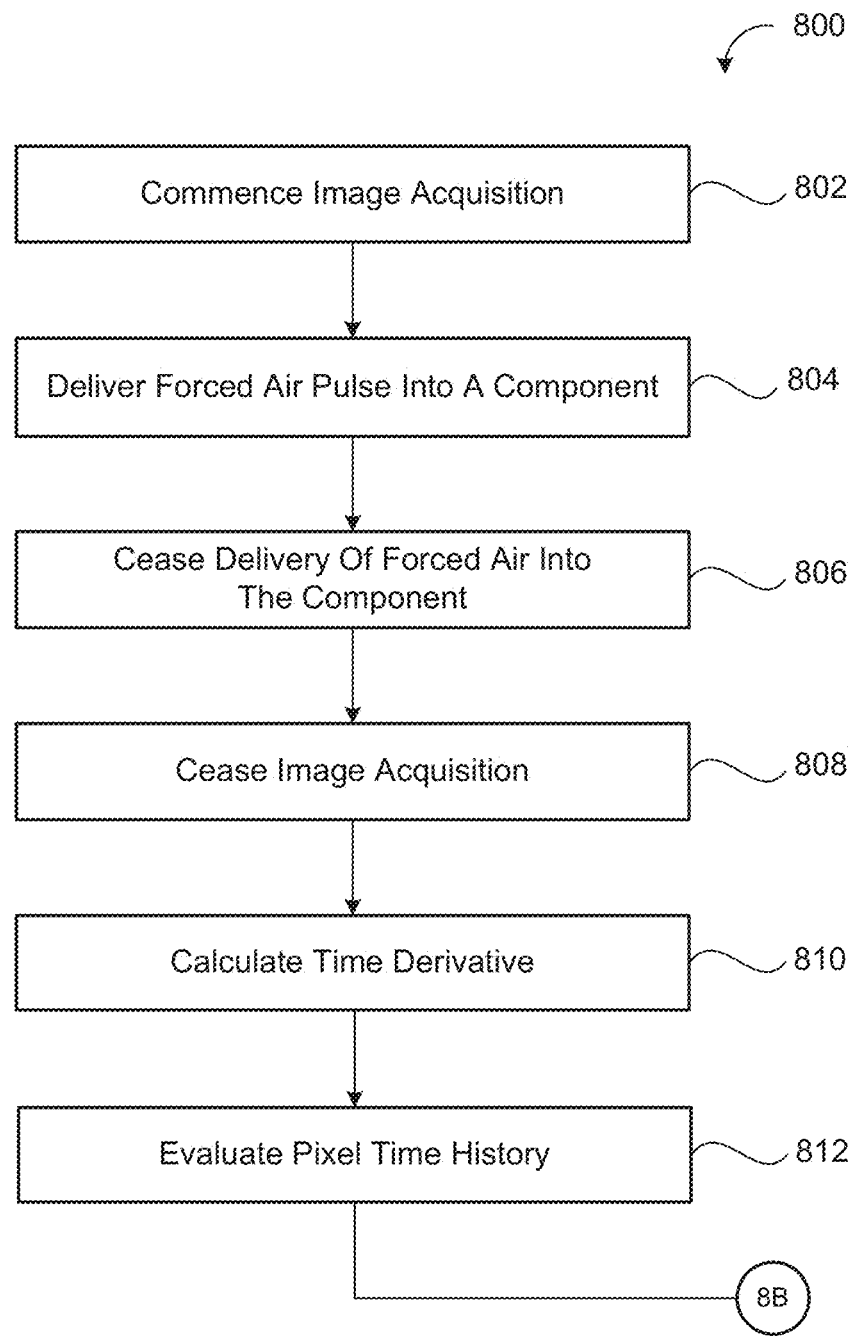
FIGS. 8A and 8B provide an exemplary arrangement of operations for thermographically testing an object.
Figure 8B:
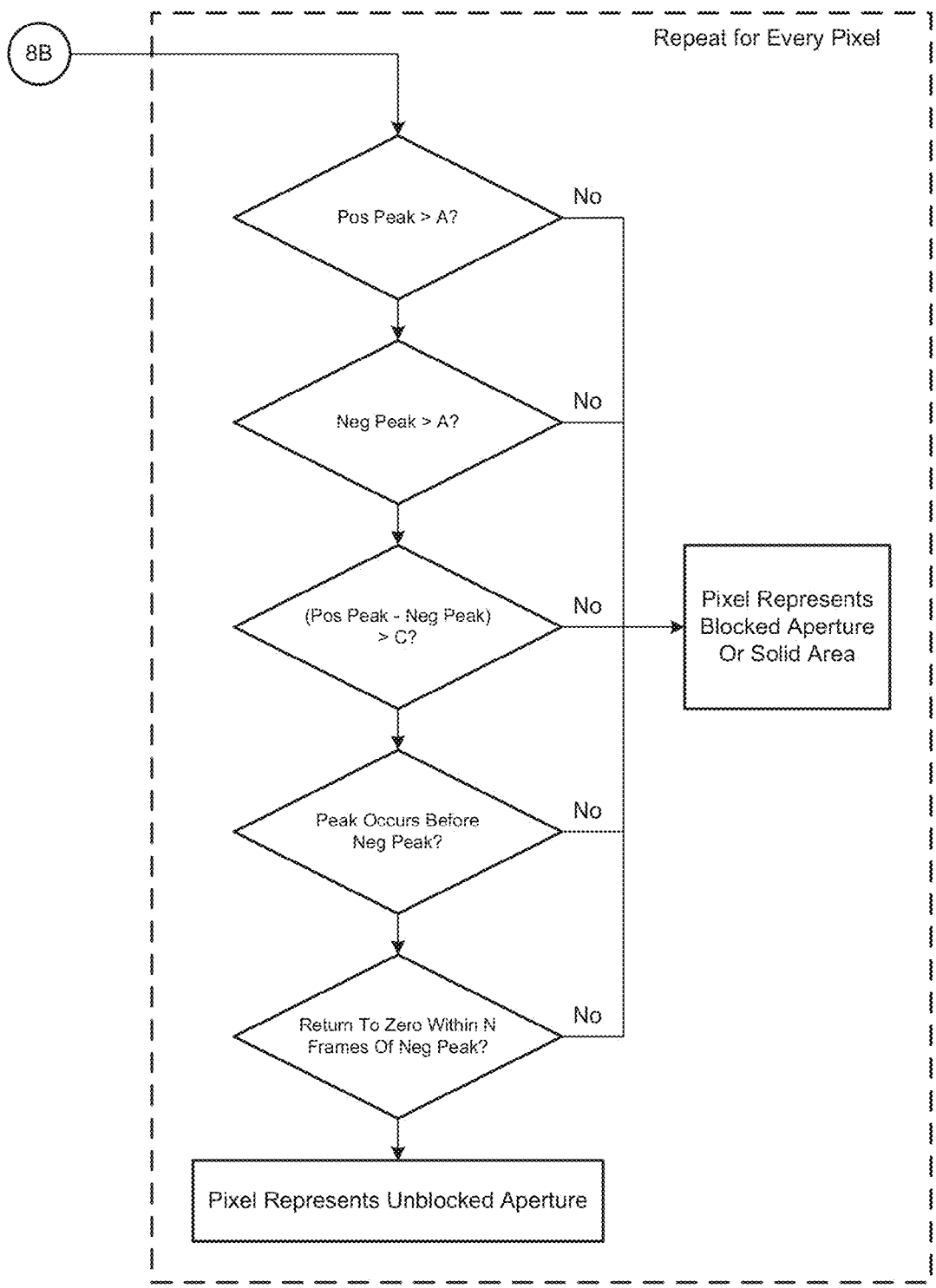

FIGS. 8A and 8B provides an exemplary arrangement 800 of operations for thermographically testing a component at least one internal passageway. In general, the method includes delivering a brief pulse of a gas (e.g., air or other suitable gas) at room temperature or any other stable temperature through the component to detect blocked internal passageways. Unlike most forced air approaches, the method may neither depend on, nor require any information about the input or output air temperature. Instead, the method may include monitoring the dynamic temperature response of the component as the airflow is first introduced and then shut off.

In the examples shown in FIGS. 9A-9E, the thermographic testing operations are applied to the turbine airfoil 100. One or more of the testing operations can be performed or controlled by the computing device 720. The system 700 can detect the near-instantaneous heating and cooling temperature responses in an immediate vicinity of an unblocked hole 122 of an exit passageway 120 to automatically detect blocked and unblocked holes 122. With additional reference to FIG. 7, the operations include commencing 802 image acquisition by the infrared camera 710. In an initial state, as shown in FIG. 9A, the airfoil 100 receives no air flow from the system 700 (e.g., from an air delivery line 750 in communication with the valve 740) and the airfoil 100 is in thermal equilibrium with its surrounding environment. The infrared camera 710 may collect a continuous sequence of digital images 712 the airfoil 100. The camera may operate at a frame rate fast enough to sample a transient ascending and descending temperature responses of the airfoil 100. In some implementations, the camera operates at a frame rates of at least 150 Hz, and in some examples at about 300 Hz. While higher rates are acceptable, results become progressively degraded at frequencies less than 150 Hz.

Referring to FIGS. 8A and 9B-9D, the operations include delivering 804 a forced air pulse or pressurized airflow into the airfoil 100. The air fills the inlet and exit passageways 110, 120 of the airfoil 100. Substantially immediately after the onset of air flow into the airfoil 100, static air in the airfoil 100 and the delivery line 750 compresses and causes a temperature increase of the internal surfaces of the inlet and exit passageways 110, 120 of the airfoil 100, as illustrated in FIG. 9C. The duration of the compression heating is typically quite brief (e.g., on the order of tens of milliseconds), and determined by the volume of static air in the airfoil 100 and delivery line 750, the number, size and distribution of passageways 110, 120 and exit holes 122, and the pressure of the incoming air. The duration of the compression heating can be adjusted by changing a length or diameter of the delivery line 750. Although the operations include delivering a pulse of air, the inspection can also be performed by continuously delivering a flow of air to the air foil 100 and modulating the air flow delivery, such as by using a step function or other pulsing effect. The compressed air escapes through the exit passageways 120, as illustrated in FIG. 9D.

The sudden introduction of a relatively high pressure gas stream into the fixed volume of the passageways 110, 120 of the airfoil 100, which is in equilibrium with its environment at room temperature, causes substantially instantaneous compression of the static air initially present in the passageways 110, 120, and thus heating of the air. As that heated volume of air is expelled through the exit passageways 120 of the airfoil 100, exterior airfoil surfaces 102 near exit holes 122 of the exit passageways 120 can be heated by convective contact (FIG. 9D). Once the original static air volume has been expelled, it is replaced by a steady flow of relatively cooler pressurized air, which is expelled through the exit passageways 120 at a steady rate. The initial temperature rise that occurred as a result of gas compression is quenched by a combination of conduction of the heat generated at the exterior airfoil surface 102 into the interior of an associated airfoil wall 104 of the airfoil 100, and convective cooling by the subsequent steady state airflow.

Referring to FIGS. 7, 8A and 9E, the operations further include ceasing 806 delivery of the air flow to the airfoil 100, and then ceasing 808 image acquisition from the infrared camera 710. As the forced airflow is substantially instantaneously shut off, the airfoil 100 experiences a sudden decrease in internal air pressure, which results in a sudden temperature drop of the air and/or the airfoil 100. Air in the airfoil 100 may expand into the delivery line 750, resulting in a drop in internal airfoil pressure.

Referring again to FIG. 7, in some examples, the computing device 720 receives a continuous sequence of thermal images 712 of at least an exit hole 122 defined by the at least one internal passageway 120 at a surface 102 of the airfoil 100. The computing device also causes the air source 730 to deliver a pressurized airflow pulse into the at least one internal passageway 110, 120 of the airfoil 100 and to cease delivery of the airflow pulse. The computing device 720 determines a temperature response signal as function of time based on the received thermal images 712, a first derivative 1001 of the temperature response signal 1000, and a level of blockage of the at least one internal passageway 110, 120 based on the first derivative 1001 of the temperature response signal 1000.

Figure 10A:
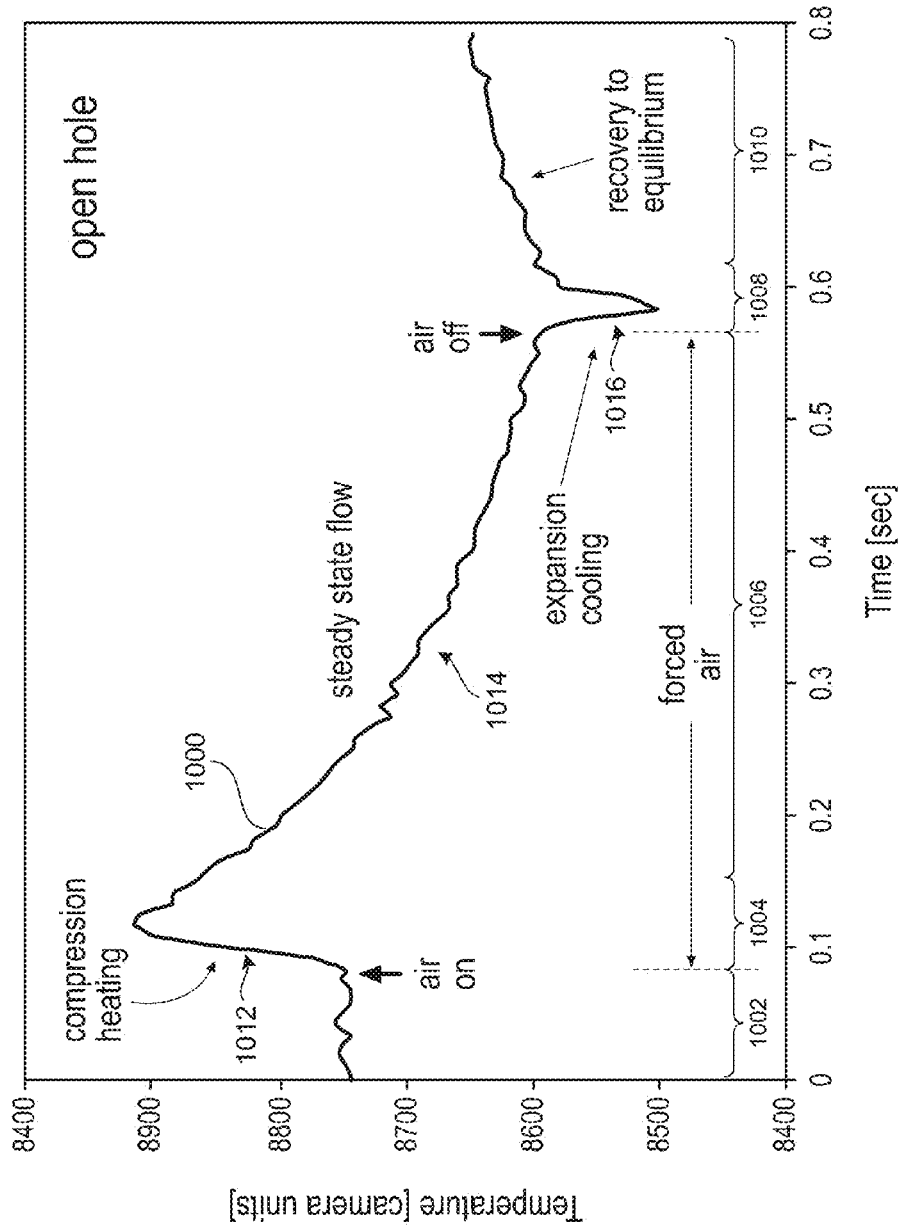
FIGS. 10A and 10B are graphical views of exemplary temperature response signals for an unblocked passageway or hole.
Figure 10B:
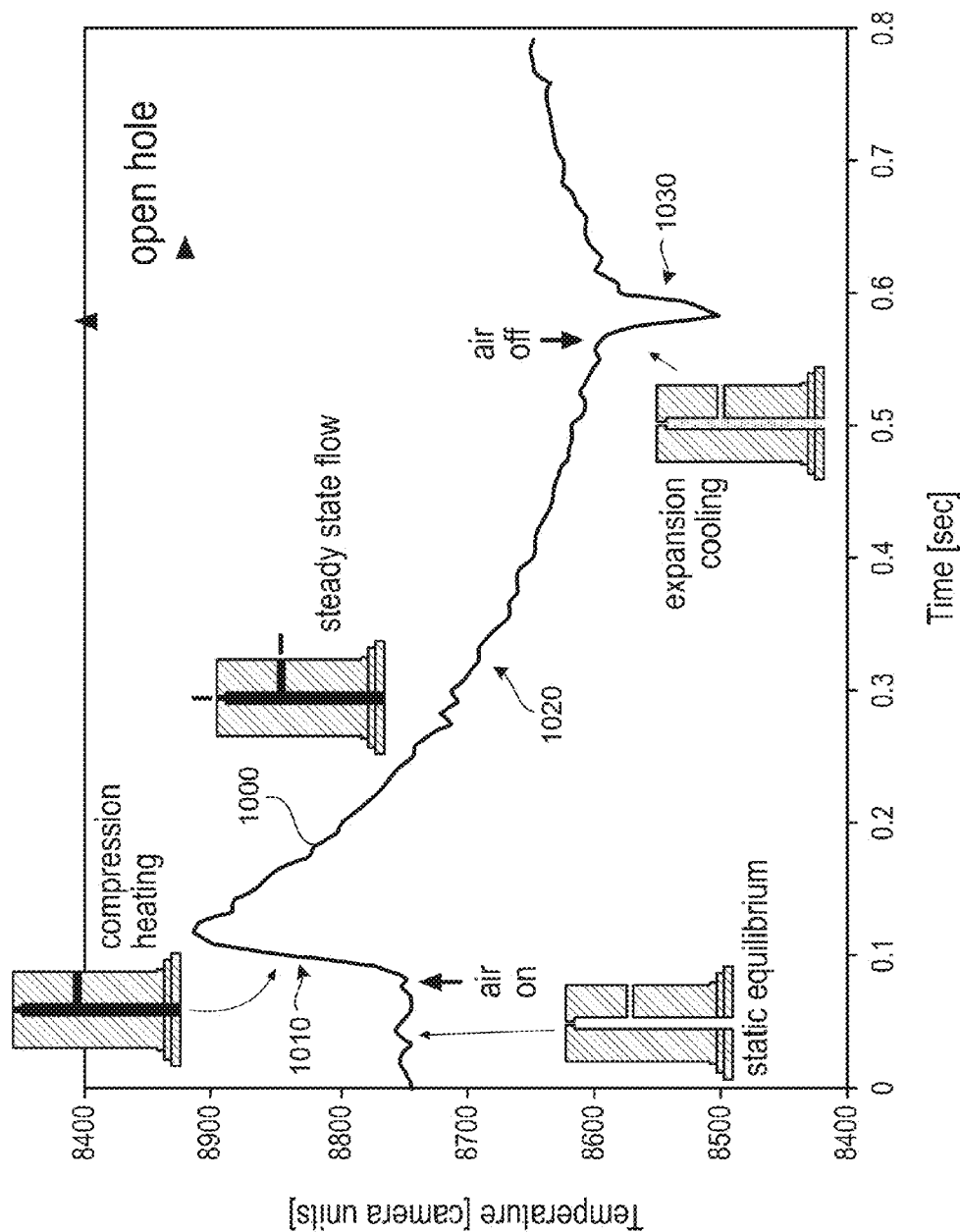
Figure 10C:
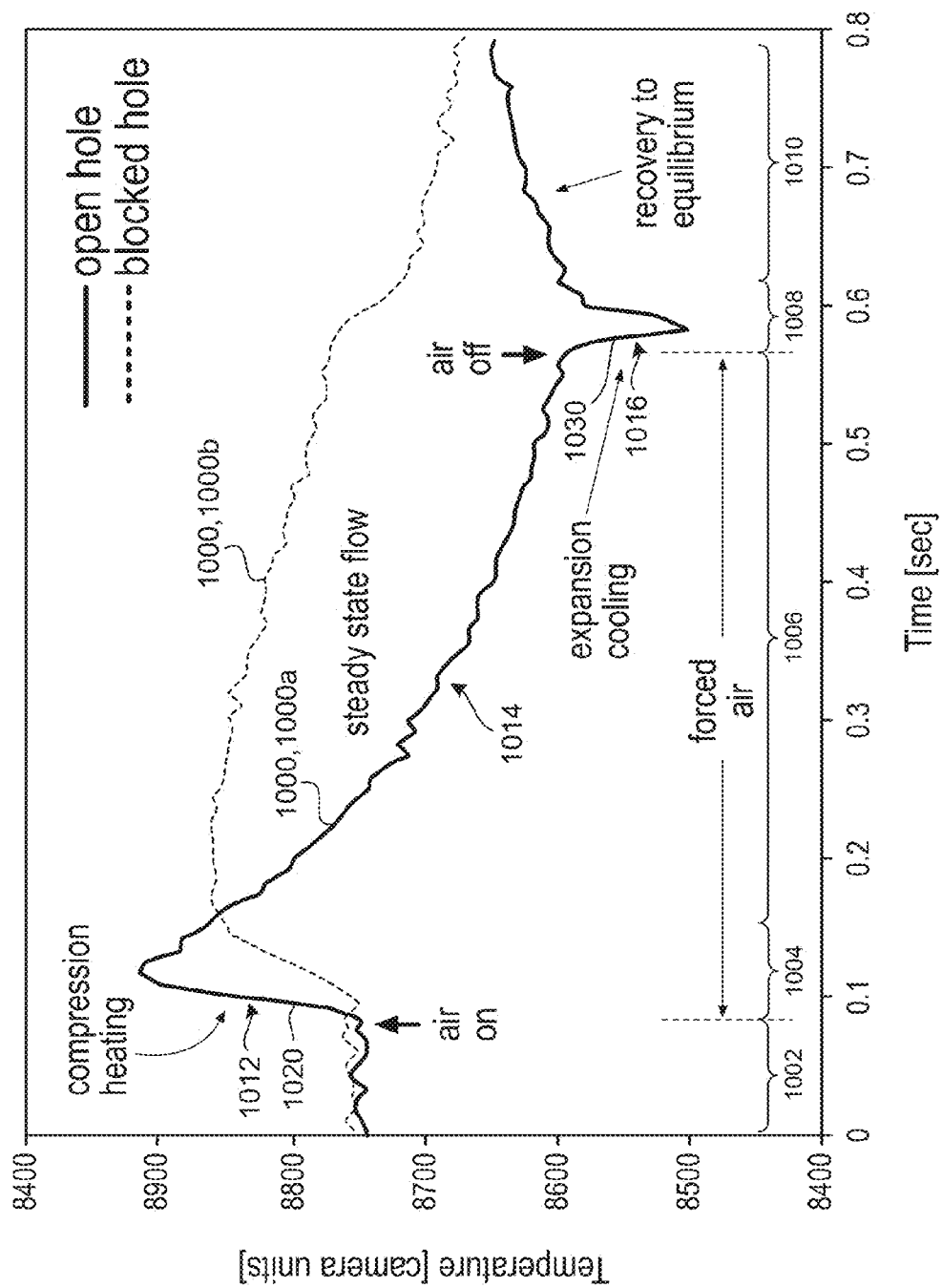
FIG. 10C is a graphical view of exemplary temperature response signals for an unblocked hole and a blocked hole.

Referring to FIGS. 7 and 10A-10C, the infrared camera 710 may capture images 712 of the airfoil 100 before, during, and after delivery of the air pulse. The net effect of the air delivery process on a surface temperature of the airfoil 100 in the immediate vicinity of an exit passageway hole 122 is a sudden temperature increase (e.g., due to expulsion of the original static gas), followed by a gradual temperature decrease (e.g., due to conduction and convection), and then a sudden temperature drop (e.g., due to decompression at shut-off). The entire process results in a predictable temperature response signal 1000 detectable by the infrared camera 710, as illustrated in FIGS. 10A-10C, providing exemplary graphs of a temperature response signal 1000 as a function of time. The surface temperature of the exterior airfoil surfaces 102 about an exit passageway hole 122 is at an equilibrium temperature with its environment during a first time period 1002 of the thermographic testing before any air delivery to the airfoil 100. During a second time period 1004, the surface temperature of the airfoil 100 in the immediate vicinity of the monitored exit passageway hole 122 suddenly increases due to compression of the static air inside the airfoil 100 and delivery of the compressed air pulse into the airfoil 100. The sudden temperature increase has a corresponding temperature peak 1012 on the temperature response signal 1000. The compression air is then expelled through the corresponding exit passageway 120. During a third time period 1006, the airfoil 100 experiences a gradual temperature decrease due to conduction and convection of the heat generated by initially compressing the air inside the airfoil passageways 110, 120. As a result, a portion 1014 of the temperature response signal 1000 corresponds to a gradual temperature decrease or a negative slope. Upon ceasing delivery of the air flow into the airfoil 100, the airfoil 100 experiences a sudden temperature drop during a fourth time period 1008, due to decompression and expansion of the air inside of the airfoil 100. The sudden temperature decrease has a corresponding temperature dip 1016 on the temperature response signal 1000. During a fifth time period 1010, the temperature of the airfoil 100 and the air inside the airfoil 100 return to equilibrium with the surrounding environment.

Referring to FIGS. 7-10C, the testing operations further include determining 810 a time derivative of a temperature response signal 1000 as a function of time and evaluating 812 a pixel time history for each pixel 714 of the camera 710 to identify positive and negative derivative peaks corresponding to the sudden temperature increase and subsequent sudden decrease. With additional reference to FIGS. 17A and 17B, the operations may include identifying image pixels 714 corresponding to positive derivative peaks 1007 immediately followed by negative derivative peaks 1009 for identifying the temperature peak 1012 corresponding to the onset of the forced air pulse, where both derivative peaks 1007, 1009 are greater than a threshold peak value A. The threshold peak value A can be determined separately for each test component or a standard value can be used. The operations can also include identifying image pixels 714 corresponding to negative derivative peaks 1009 immediately followed by positive derivative peaks 1007 for identifying the temperature dip 1016 corresponding to the shut-off of the forced air pulse, where both derivative peaks 1007, 1009 are greater than a threshold peak value B. This threshold peak value B can be the same as or different from the threshold peak value A used for identifying the temperature peak 1012. Moreover, the threshold peak values A, B may be determined by evaluating a statistically significant number of components (e.g., air foils 100) that have been determined to be blocked or unblocked by other methods. In some implementations, the operations include identify pixels 714 where the difference between the positive and negative derivative peaks for onset and shut-off is greater than a threshold peak difference C.

The operations may optionally include determining that the derivative signal 1001 of the image pixels 714 returns to equilibrium (e.g., within an equilibrium threshold range of zero) within a threshold number of frames for identifying the fifth time period 1010 of the temperature response signal.

While the actual, or even the relative temperature of exterior airfoil surfaces 102 near an exit passageway hole 122 or near a given exit may depend on many factors, including the static and forced air temperature, airfoil temperature, pressure of the forced air, the overall graphical shape of a temperature response signal 1000 as a function of time is largely independent of these factors. An airfoil area 106 (FIG. 9E) in and immediately surrounding an unobstructed exit passageway hole 122 will display a sharp positive temperature peak 1012 substantially immediately after the onset of delivery of the air pulse, and a corresponding negative peak 1016 substantially immediately after cessation of delivery of the air flow, with a substantially gradual temperature decrease portion 1014 therebetween. In contrast, the same points on a temperature response signal 1000b associated with a blocked hole 122 will display a relatively more gradual heating and cooling curve, as illustrated in the example shown in FIG. 10C.

Referring to FIG. 10D, the operations may include associating the identified image pixels 714 having a temperature response signal 1000 satisfying the pixel time history evaluation with unblocked holes 122 and optionally marking corresponding pixel locations on a digital image 712 from the infrared camera 710. An operator may view the digital image 712 and/or the temperature response signals to determine which exit passageways 120 are open and which passageways 120 are blocked or partially blocked.

Referring again to FIG. 10C, in some implementations, a method of determining a level of blockage of an internal passageway 110, 120 includes analyzing a shapes of the temperature response signals 1000 (i.e., a signal derived from a temperature-time history of a corresponding pixel 714 of a sequence of thermal images 712 captured by the infrared camera 710) for each pixel 714 of the thermal images 712. In the example shown, the temperature response signals 1000 includes a first peak 1012 having a relatively fast rise time (i.e., a rapid increase in temperature over a relatively short period of time). The method may include identifying a first peak 1012 having monotonically rising shape or portion 1020 and/or a threshold change in temperature during a time period occurring between an onset of the air pulse and a time at which the corresponding pixel 714 attains a maximum temperature over the sampled period of time. Similarly, the method may include identify a second peak 1016 having monotonically falling shape or portion 1030 and/or a threshold change in temperature during a time period occurring between shut-off time of the air pulse and a time at which the corresponding pixel 714 attains a minimum temperature over the sampled period of time. The method may also include fitting a polynomial to at least one of the identified monotonical portions 1020, 1030 of the temperature response signal 1000 and/or comparing the temperature response signal 1000 to a reference signal 1000 corresponding to a validated component.

Figure 11:
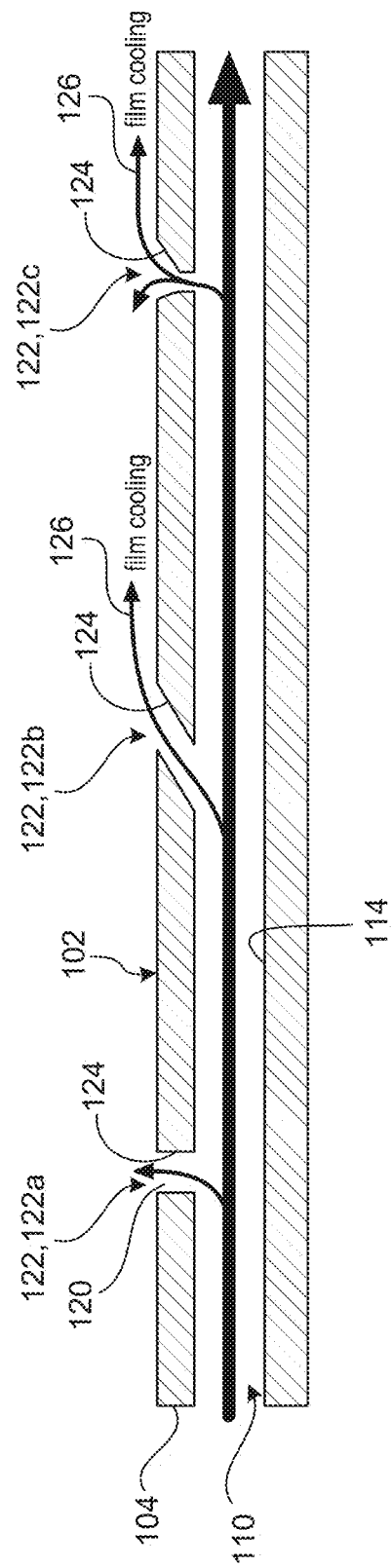
FIG. 11 is a section view of an exemplary turbine airfoil illustrating air flow paths out of different types of holes.
Figure 12:
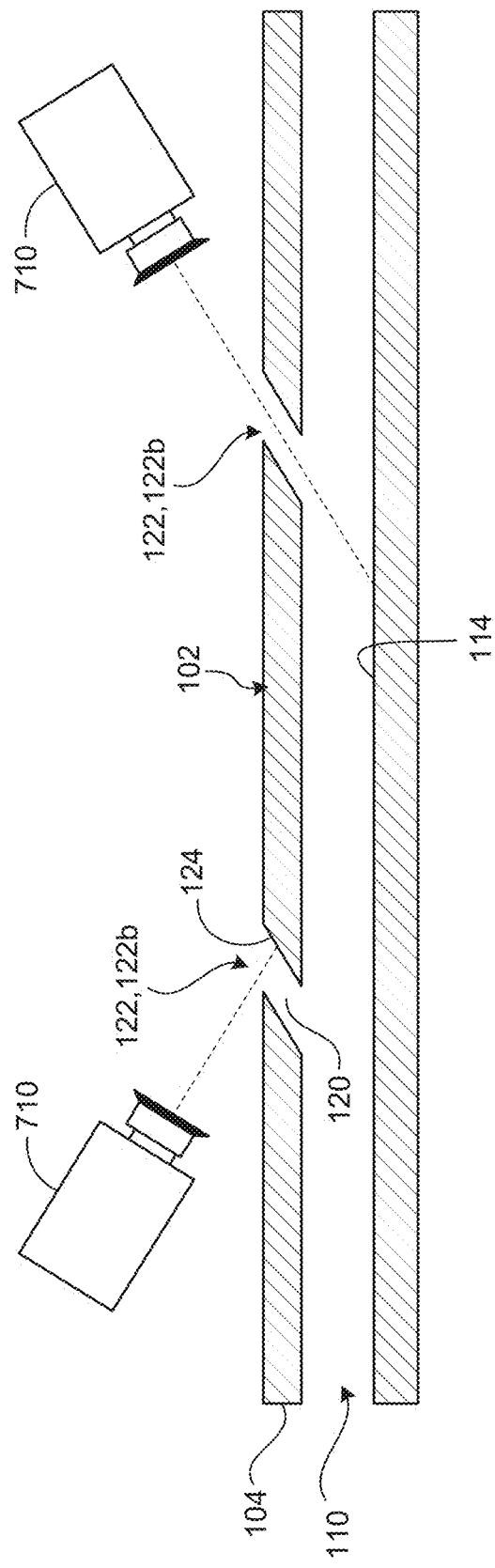
FIG. 12 is a section view of an exemplary turbine airfoil illustrating how different camera angles can obtain thermal images of internal airfoil surfaces.

FIG. 11 illustrates an exemplary airfoil 100 having a wall 104 defining different types of exit holes 122. In the example shown, the airfoil wall 104 defines a straight through exit hole 122a, where walls 124 of the corresponding exit passageway 120 are substantially normal (e.g. perpendicular) to the exterior airfoil surface 102. In some examples, the airfoil wall 104 defines an angled exit hole 122b, where the walls 124 of the corresponding exit passageway 120 are arranged at an angle with respect to the exterior airfoil surface 102. This arrangement causes exiting air to pass over the exterior airfoil surface 102 promoting surface cooling. For example, the angled holes 122b can direct a film 126 of air over the airfoil surface 102 to cause film cooling of the airfoil 100 through convection between the air film 126 and the airfoil surface 102. As a result, the angled holes 122b may provide relatively more efficient cooling of the airfoil 100 than straight through holes 122a. In yet further examples, the airfoil wall 104 defines a complex exit hole 122c, where the walls 124 of the corresponding exit passageway 120 are arranged at different angles with respect to the exterior airfoil surface 102. The complex holes 122c can be configured to cause exiting air to pass over the exterior airfoil surface 102 in multiple directions, thus creating air films 126 along multiple directions covering a relatively larger surface area than the other two types of holes 122a, 122b. Depending on a position of the infrared camera 710, the system 700 can measure infrared radiation emitted from the airfoil surface 102, walls 124 of an exit passageway 120, and walls 114, 124 of other internal passageways 110, 120, as shown in FIG. 12.

Figure 13:
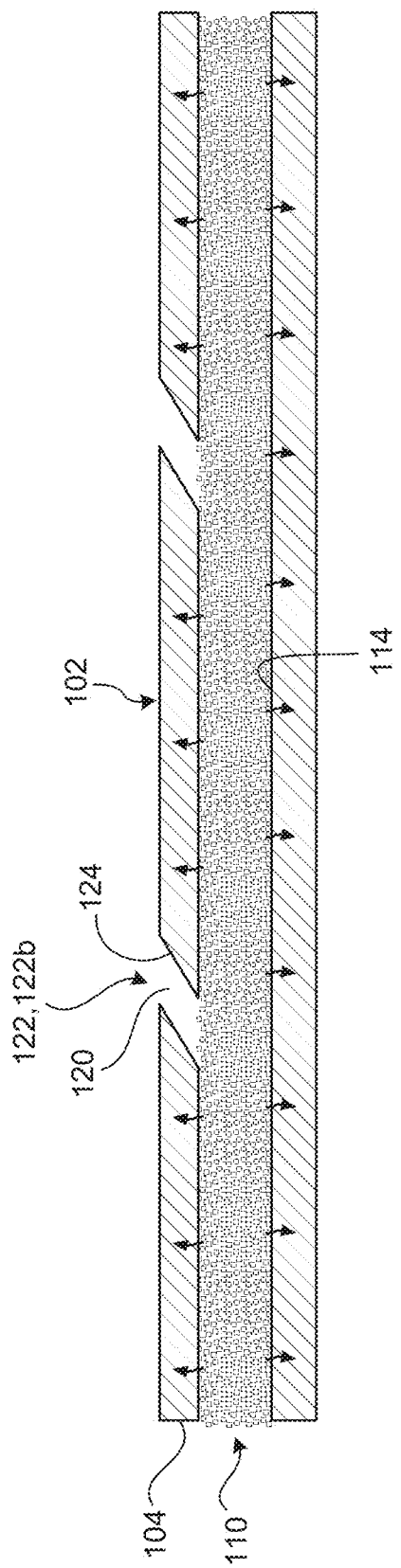
FIG. 13 is a section view of an exemplary turbine airfoil experiencing heat conduction from heated internal air through walls of the airfoil.

Referring to FIG. 13, the sudden introduction of a relatively high pressure gas stream into the fixed volume of the passageways 110, 120 of the airfoil 100 causes substantially instantaneous compression of the static air initially present in the passageways 110, 120, and thus heating of the air. The heated air heats the walls 114, 124 of at least some of the internal passageways 110, 120. The internal walls 114, 124 may consequently conduct heat from the internal passageways 110, 120 through the airfoil wall 104 to the exterior surface 102 of the airfoil 100. A transit time of the heat conduction may depend on a thickness and/or composition (e.g., thermal diffusivity) of the airfoil wall 104.

Figure 14:
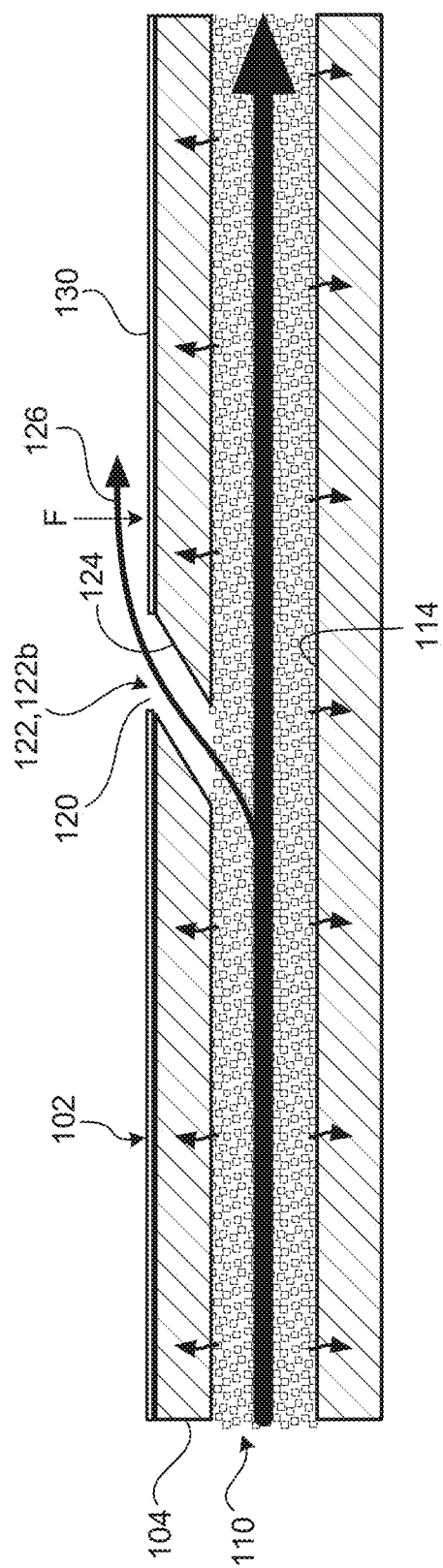
FIG. 14 is a section view of an exemplary turbine airfoil having an external surface film that experiences film heating due to heated air exiting though an angled exit passageway.

Referring to FIG. 14, in some implementations, an external surface 102 of the airfoil 100 (and/or a thermal barrier coating 130 thereon) receives a film 126 of expelled air from an angled exit hole 122b, for example. The expelled air film 126, when heated, can heat the external airfoil surface 102 through convection (or the thermal barrier coating 130, which conducts heat to the airfoil wall 104). For example, at a point F on the exterior airfoil surface 102 near the exit hole 122, 122b and in a path of the airflow, the expelled airflow can create an air film 126 across the exterior airfoil surface 102 (e.g., across the thermal barrier coating 130) which heats the exterior airfoil surface 102 through convection with the received airflow. Moreover, conduction of heat through the airfoil wall 104 can further heat the exterior airfoil surface 102.

Figure 15B:
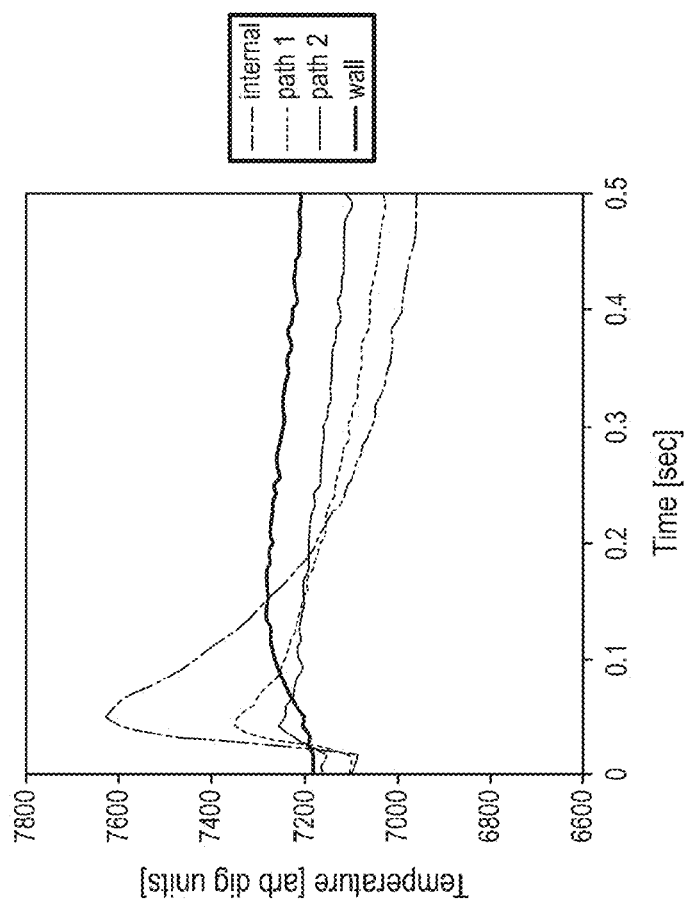
FIG. 15B is graphical view of temperature response signals corresponding to the heat transfer paths shown in FIG. 15A.
Figure 15A:
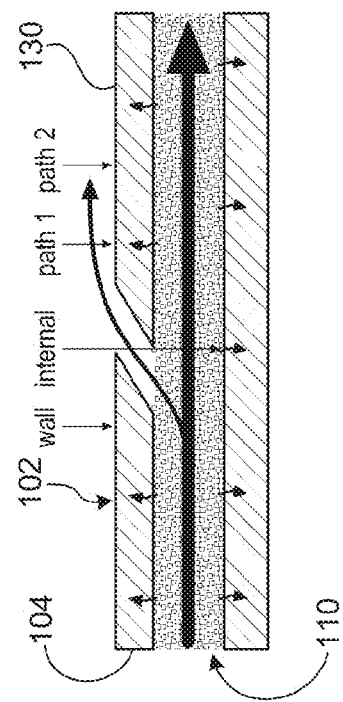
FIG. 15A is a section view illustrating different heat transfer paths through an exemplary turbine airfoil.

Referring to FIGS. 15A and 15B, the airfoil 100 may experience different modes or paths of surface heating due to the heated internal air. In the example shown, the airfoil 100 can experience heating by conduction through the airfoil wall 104, internal core heating by conduction, film heating by convection of a received airflow out of an exit hole 122 and over the thermal barrier coating 130, and a combination of localized film heating and airfoil wall conduction near an exit hole 122. For a brief period of time after the introduction of compressed air into the airfoil 100, film heating of the exterior airfoil surface 102 (e.g., via) may dominate as the surface heating mode for the airfoil 100. After that brief period of time, other modes of surface heating may dominate.

Figure 16A:
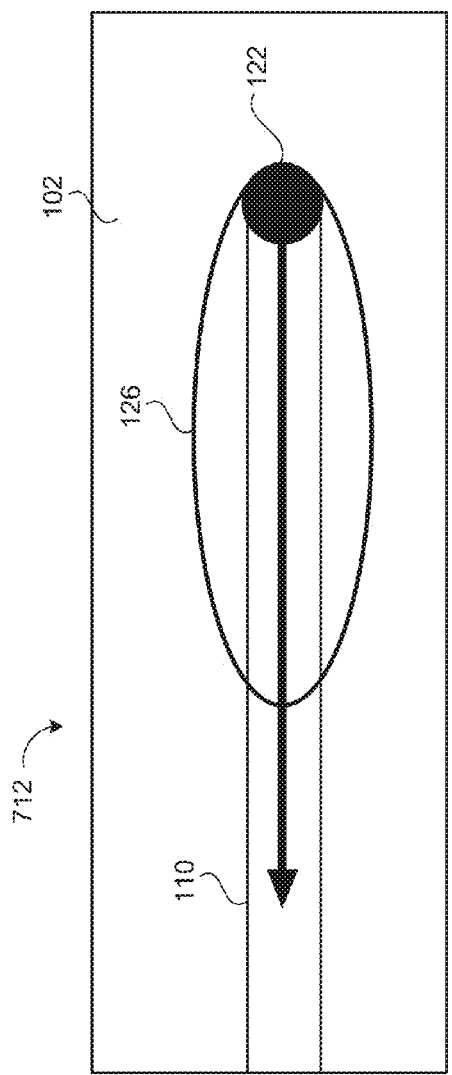
FIG. 16A is a schematic view illustrating an exemplary film heating path from an airfoil hole over an external surface of an airfoil.
Figure 16B:
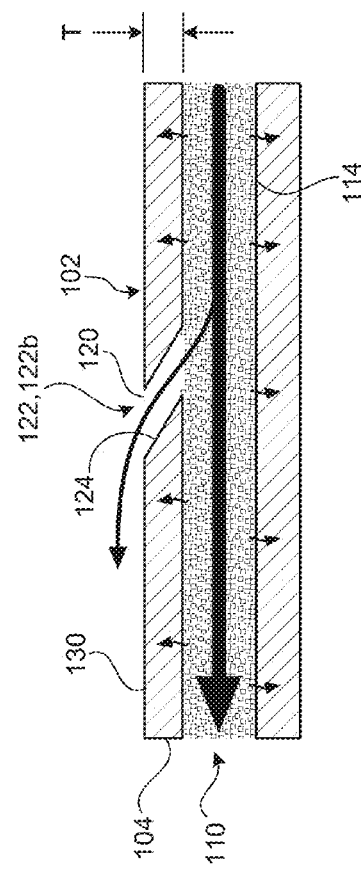
FIG. 16B is a section view of an exemplary turbine airfoil illustrating an airflow exit path from an airfoil hole corresponding to the film heating path shown in FIG. 16A.

FIGS. 16A and 16B illustrate an example where the shape of a heated air film 126 on the exterior airfoil surface 102 can be captured on a thermal image 712 (FIG. 16A) of a corresponding airfoil 100 (FIG. 16B). Initial escapement of the heated internal air may cause heating of the exterior airfoil surfaces 102 about the corresponding exit hole 122. Moreover, later steady state flow relatively cooler air may cause cooling of those exterior airfoil surfaces 102. Air escaping through an exit hole 120 can be directed by the exit hole 120 (e.g., by an angled exit hole 122b or a complex exit hole 122c) over the airfoil surface 102. The exit hole 122 can be arranged or configured (e.g., constructed with a specific shape) to create certain shape of air film 126 on the air foil surface 102, such as an elliptical shape, fan shape, or other suitable shape. The thermographic inspection of the airfoil 100 may include analysis of the shape of the thermally detected air film 126 (e.g., shape of air film in a thermal image 712) to determine whether the corresponding exit hole 122 meets a specification. For example, a detected thermal shape of the air film 126 can be compared against reference shapes of air films corresponding to properly formed exit holes 122. The inspection may include receiving or determining a temperature response signal 1000 as function of time for each corresponding pixel 714 of the received thermal images 712 from the infrared camera 710 and determining the shape of the air film 126 based on the temperature response signals 1000. During operation of the air foil 100, the expelled air film 126 acts to cool the hot airfoil surface 102. Since the inspection is performed on an air foil 100 at room temperature, the expelled air heats the air foil surface 102, thus allowing thermographic detection and inspection of the air film shape.

Figure 17A:
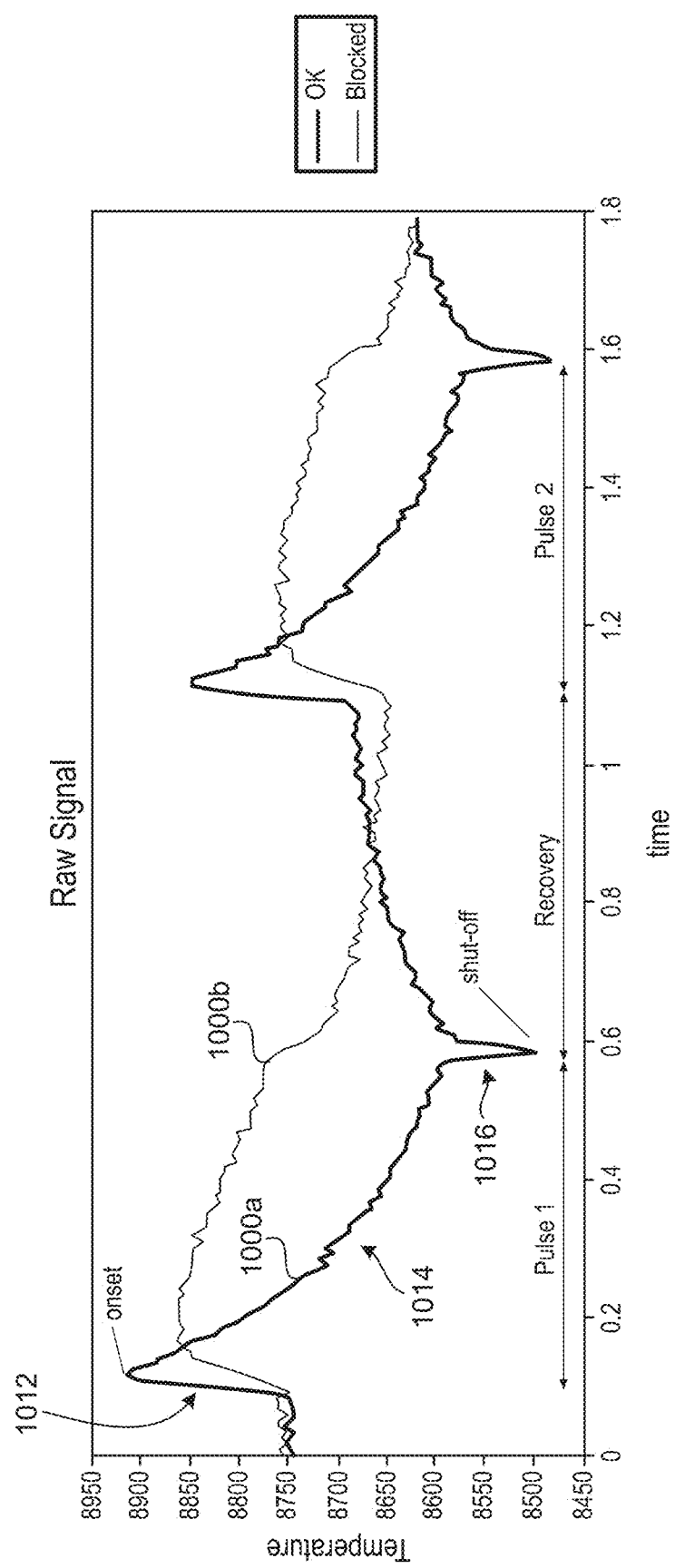
FIG. 17A is graphical view of an exemplary temperature response signal of a thermographic testing system for multiple sequential air pulses into a turbine airfoil.
Figure 17B:
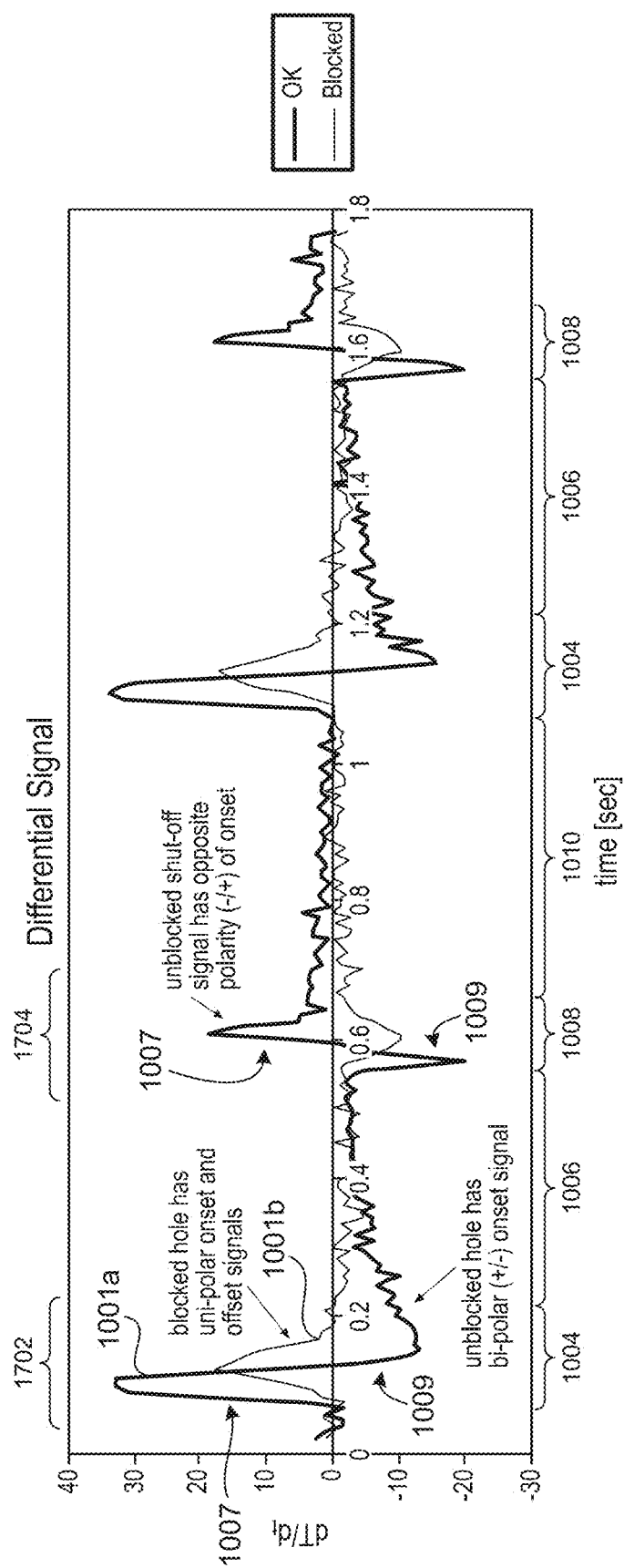
FIG. 17B is graphical view of a first derivative of the temperature response signal shown in FIG. 17A.

In some implementations, the operations for thermographically testing the airfoil 100 (or another component) includes delivering a sequence of several air pulses (e.g., 2-3) to confirm repeatability of the test results. The first air pulse can be used to help seat the airfoil 100 in a test fixture and may be discarded, as some motion of the airfoil 100 may occur due to the initial application of forced air. The airfoil 100 may be imaged by the infrared camera 710 either directly, or using mirrors, so that top, bottom, side, and/or edge surfaces of the airfoil 100 may be tested simultaneously. FIG. 17A provides exemplary graphs of a first temperature response signal 1000a for an unblocked passageway 110, 120 and second temperature response signal 1000b for a blocked passageway 110, 120. FIG. 17B provides exemplary first derivatives 1001a, 1001b of the temperature response signals 1000a, 1000b shown in FIG. 17A. In this example, the testing system 700 delivers two sequential air pulses to the airfoil 100, while acquiring thermal images 712 of the airfoil 100 using the infrared camera 710. Both air pulses result in repeatable temperature response signals 1000a, 1000b.

A degree of blockage of a passageway 110, 120 can be determined by comparison of a peak amplitude of the temperature response signal for a test airfoil 100 to a peak amplitude of the corresponding temperature response signal for the reference airfoil 100. In the example shown in FIG. 17A, the first temperature response signal 1000a is of a reference airfoil 100 have known or otherwise verified unblocked passageways 110, 120, while the second temperature response signal 1000b is of a test airfoil 100. Analysis of the corresponding first derivative signals 1001a, 1001b shown in FIG. 17B reveals that the first derivative signal 1001b of the tested airfoil 100 has uni-polar onset and shut-off signal portions 1702, 1704 (i.e., has only a positive peak 1007 or a negative peak 1009), signifying a blocked passageway 110, 120. In contrast, the first derivative signal 1001a of the reference airfoil 100, which has a bi-polar onset signal portion 1702 (i.e., has a positive peak 1007 followed by a negative peak 1009) and bi-polar shut-off signal 1704 (i.e., has a negative peak 1009 followed by a positive peak 1007) opposite in polarity from the onset signal portion. Moreover, the onset signal portion 1702 of the first derivative signal 1001b of the tested airfoil 100 has a positive peak 1007 with an amplitude less than the threshold peak value A (e.g., 25) and no negative peak 1009 (e.g., has an amplitude less than the threshold peak value A). The positive and/or negative peak amplitudes can be used to determine a level of passageway blockage, for example, based on a one-to-one correspondence of amplitude to blockage or other relationships. The onset and shut-off signal portions 1702, 1704 occur during the corresponding second and fourth time periods 1004, 4008.

For evaluating 812 the pixel time histories, the threshold values A, B, N may be established using the reference airfoil 100 or a component having verified unblocked passageways 110, 120. Moreover, the operations can be performed automatically using an automated system. The testing operations can provide a quantitative analysis of the airfoil 100 to identify, evaluate, and quantify localized blockages. Rather than looking at a net air flow to determine that there is a blockage and not necessarily a location of the blockage does not allow for easy reworking or repair of a blocked airfoil 100. Since the testing method does not require control or monitoring of inlet or outlet temperatures or pressures, the testing system 700 can operate in just about any environment and does not require determining a net energy balance or precise control and monitoring of environmental or air parameters. Moreover, the testing method does not require precise radiometric temperature measurement. Instead, the testing method analyzes the shape of the temperature-time history of each image pixel 714, not necessarily the amplitude. As such, emissivity of the airfoil may vary, or be less than ideal.

In some implementations, the testing system 700 can be used to determine blockage levels of internal structures and/or inspect internal cavities that have no exit holes on the airfoil surface and terminate within the airfoil 100. While much of the compressed heated air escapes through passageways 120 having exit holes 122, the heated air may convectively heat other internal structures of the air foil 100. As illustrated in FIG. 16B, heat from the heated internal walls 114, 124 of the airfoil 100 may propagate toward the cooler exterior surface 102 of the airfoil 100 through the process of thermal diffusion. The time required for heat to diffuse through the airfoil 100 wall can be determined by the thermal diffusivity of the material (e.g., metal or superalloy) of the airfoil 100 and a local thickness T of the airfoil wall 104.

The process of compressed air heating causing thermal diffusion through the airfoil wall 104, and ultimately, a temperature rise at the exterior surface 102 of the airfoil 100 allows determination of changes in airfoil wall thickness T. In examples where the airfoil 100 comprises a homogeneous superalloy structure, thermal diffusivity may be relatively constant throughout the airfoil 100. Moreover, changes in a propagation time for heat to diffuse through the airfoil wall 104 and/or a maximum amplitude of the airfoil surface temperature can be associated with changes in airfoil wall thickness T along the airfoil 100.

Figure 18A:
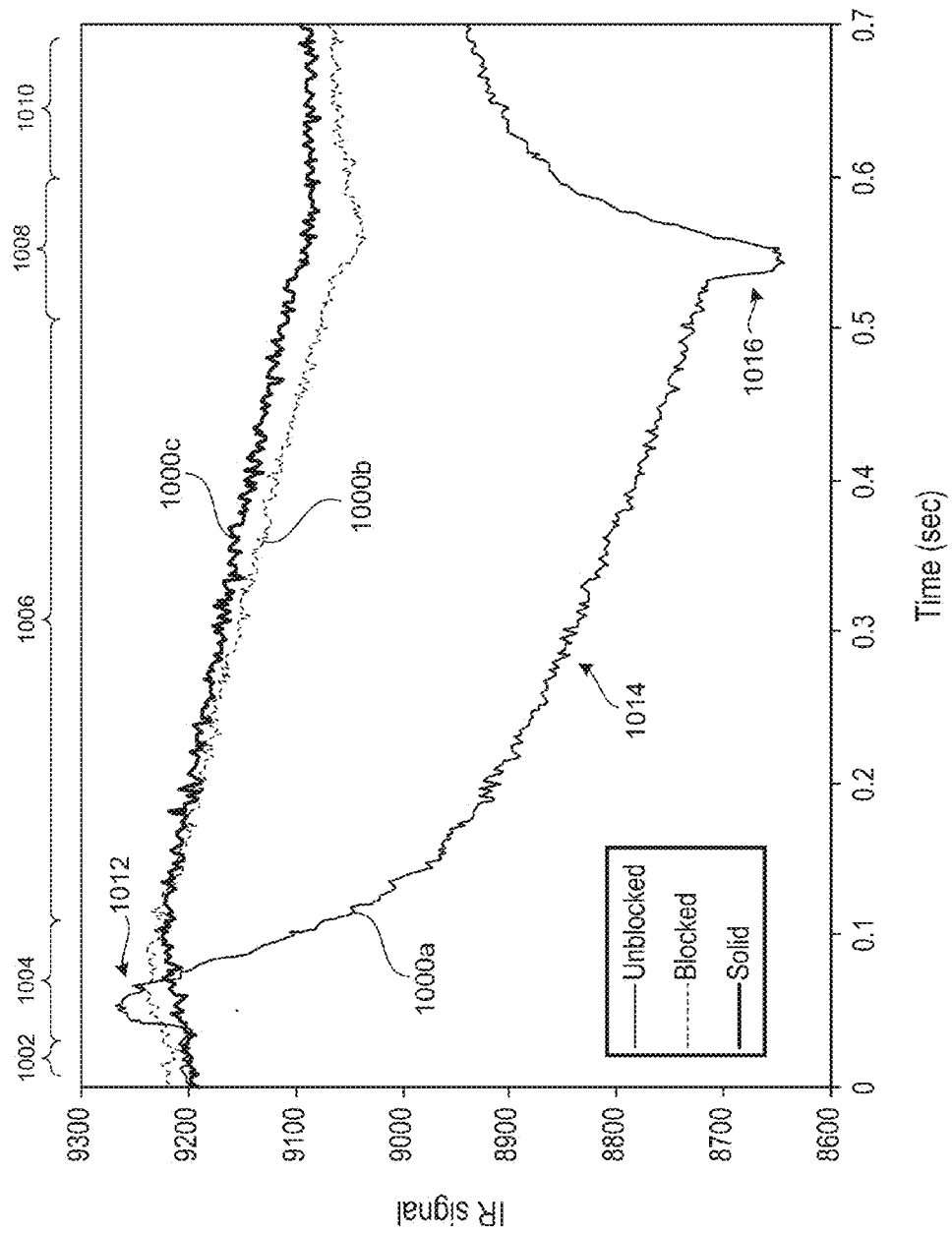
FIG. 18A is graphical view of exemplary temperature response signals of a thermographically tested turbine airfoils having a blocked hole, an unblocked hole, and a solid surface.
Figure 18B:
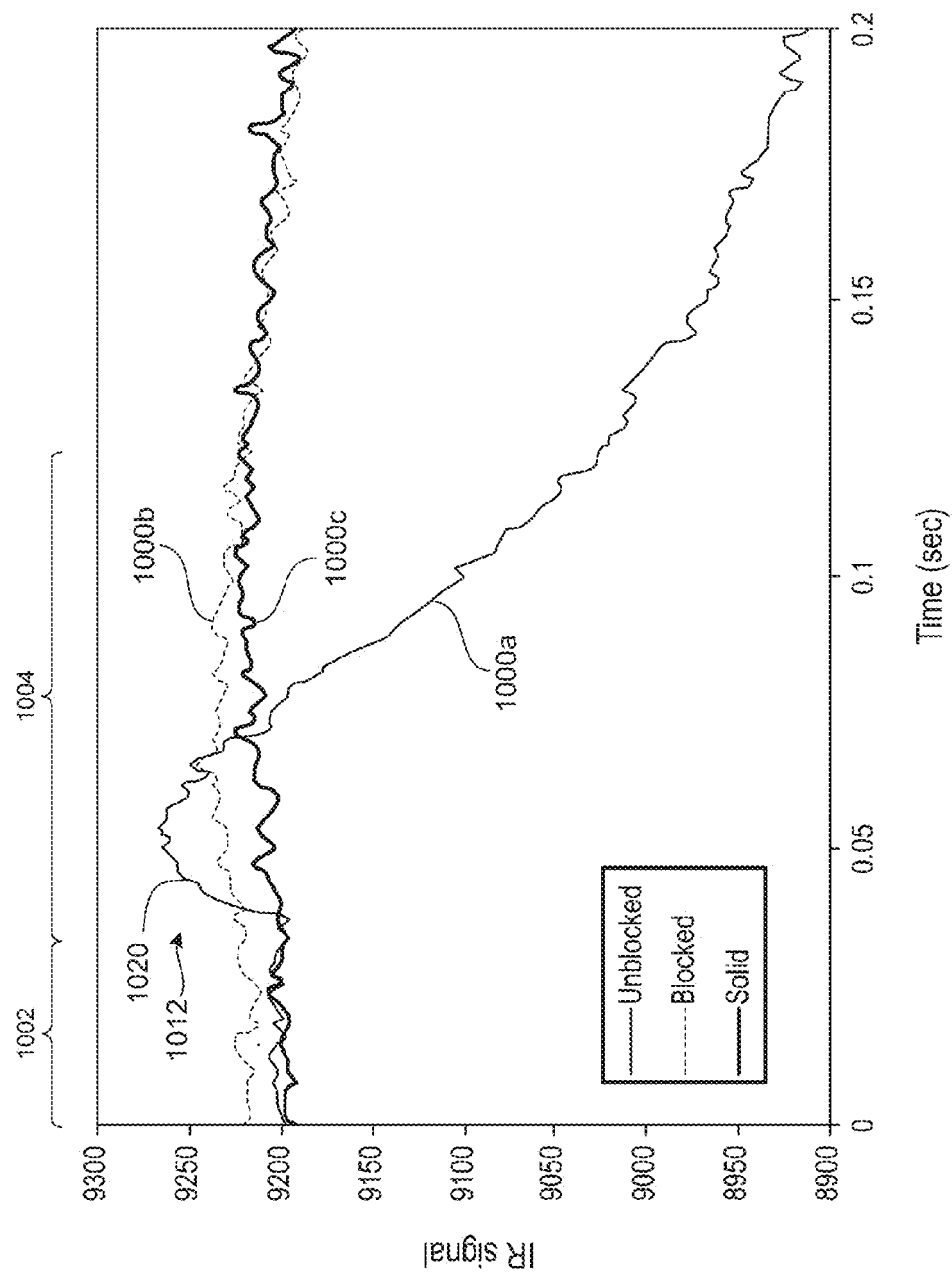
FIG. 18B is a graphical view of a portion of the temperature response signals shown in FIG. 18A illustrating a monotonically rising signal portion for the temperature response signal of the unblocked hole.

FIG. 18A provides exemplary temperature response signals 1000a, 1000b, 1000c for an unblocked hole 122, a blocked hole 122, and a solid exterior airfoil surface 102, respectively. The corresponding data was collected from the infrared camera 710 operating at a frame rate of about 500 Hz for a capture time of about 1 second for an airflow duration of about 500 milliseconds having an airflow start pressure of about 128 psi. FIG. 18B illustrates the second time period 1004 of the temperature response signals 1000a, 1000b, 1000c shown in FIG. 18A, which occurs during a compression-dominated time regime. During and immediately after the second time period 1004, the compression heating period, the surface temperature of the airfoil 100 monotonically rises. In the example shown, the monotonic temperature rise occurs over a period of about 14 milliseconds during the compression heating period or the second time period 1004. The monotonically rising portion 1020 of the temperature response signal 1000 can be enhanced by thermographic signal reconstruction (TSR), a process which allows viewing of noise free time derivatives of the temperature response signal 1000 and significantly enhances the sensitivity of the temperature response signal 1000 to small changes. Details on the TSR process and other features combinable with this disclosure can be found in U.S. patent application Ser. No. 10/848, 274, filed on May 18, 2004 (issued as U.S. Pat. No. 7,724, 925), which is hereby incorporated by reference in its entirety. After the second period 1004, the surface temperature falls during the third time period 1006 due to the steady state airflow through the internal passageways 110, 120 and convective cooling of the exterior airfoil surface 102 by the exterior environment (which may be at room temperature). The entire process can be observed and recorded with the infrared camera 710 (FIG. 7) operating at a frame rate sufficiently fast to capture the transient heating period (e.g., at a frame rate of at least 150 Hz).

Infrared images 712 of the airfoil 100 captured during thermographic testing can be analyzed for determining changes in airfoil wall thickness T. Attachments to the internal cooling channel wall which effectively change the wall thickness, e.g. pillars, posts or turbulators, all designed to control convective airflow in the cooling channels, may appear in the infrared images 712 during this period. Examination of the images 712 may be performed to confirm that these structures were cast properly.

Figure 19:
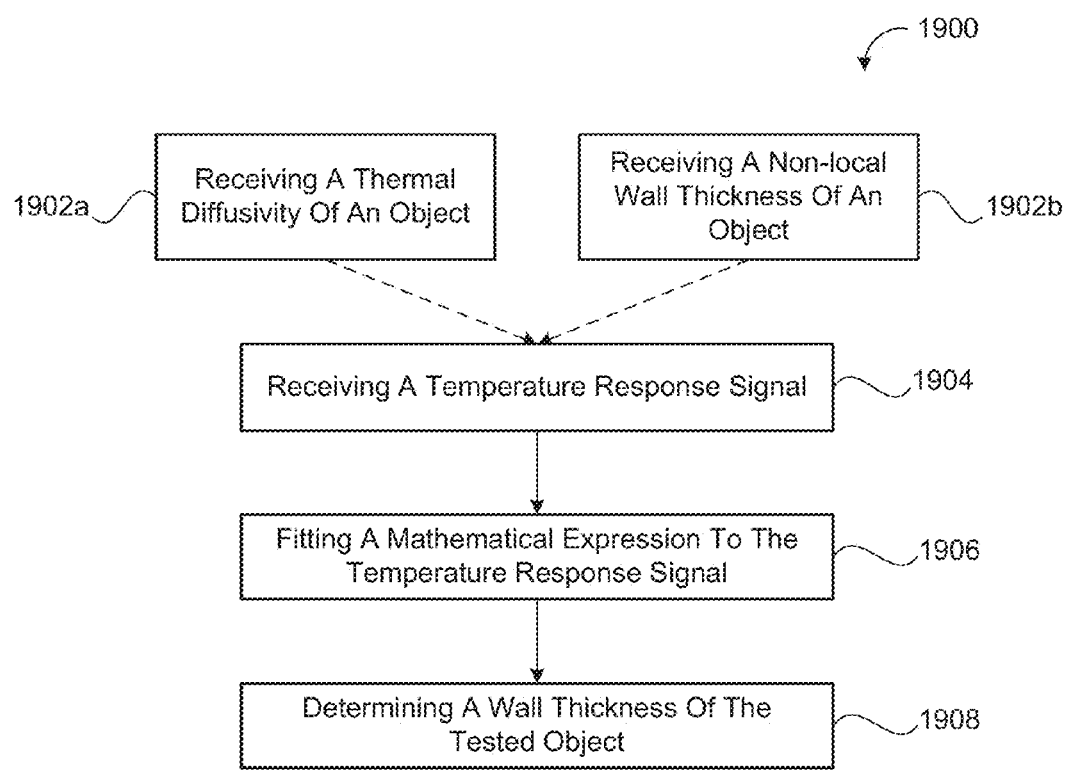
FIG. 19 provides an exemplary arrangement of operations for determining a local wall thickness of an object having internal channels.

FIG. 19 provides an exemplary arrangement 1900 of operations for determining a local wall thickness T of an object having internal channels, such as an airfoil 100. The operations include receiving 1902a a thermal diffusivity of the object or receiving 1902b a non-local wall thickness T of the object. The operations also include receiving 1904 a temperature response signal 1000 (temperature change as a function of time) for the object and fitting 1906 a mathematical expression to the temperature response signal 1000 for one-dimensional diffusion through a plate subjected to instantaneous, uniform heating, with thickness as the free parameter. The mathematical expression may be fit to the monotonically rising portion 1020 of the temperature response signal 1000. The operations include determining 1908 a wall thickness T of the tested object. In some examples, the operations include determining a temperature response signal 100 for each corresponding pixel 714 of the received sequence of thermal images 712, identifying a location on the thermal images 712 of the at least one internal channel and determining a wall thickness between the at least one internal channel and a surface of the object.

Alternatively, the method may include measuring the time at which each point on a surface of the object (e.g., the airfoil surface 104) reaches half of its maximum temperature and determining a local wall thickness T according to:

$$\alpha = \frac{(0.139 * T^2)}{t_{half}} \quad (1)$$

where α is thermal diffusivity, T is the wall thickness, $t_{half}$ is the time at which the temperature response signal 1000 reaches ½ of its maximum amplitude.

Wall thickness determinations along can be used to confirm proper formation of internal structures of the object. For example, the wall thickness determination method can be used to verify proper casting (e.g., that the ceramic cores did not shift position during the casting process), machining, and coating of the airfoil 100 at each step of the manufacturing process. Moreover, the method can be used to determine partial or complete blockage of the internal structures.

Referring again to FIG. 6, debris 300, such as remnants of the ceramic core used to form the internal passageways 110, 120 during the casting process, may remain in the passageways 110, 120 after the chemical leaching process. The residual core may occur in many forms, e.g. pieces that become lodged in the passageways 110, 120 or exit holes 122, a layer that becomes attached to a passageway wall 114, 124, or small isolated spots that attach to the passageway wall 114, 124. The debris 300 (e.g., residual core) may affect the cooling function of the airfoil 100. For example, core debris 300 blocking or narrowing the passageways 110, 120 can reduce the cooling airflow through the passageways 110, 120. Moreover, layers of debris 300 attached to a passageway wall 114, 124 may compromise the convective heat transfer of the cooling air flow during operation of the airfoil 100.

The presence of debris 300 in any of the airfoil passageways 110, 120 can be detected using infrared thermography. In some implementations, the temperature response signal 1000 of the airfoil 100 includes identifiable qualities (e.g., peaks, shapes, etc.) for discerning a level of internal passageway blockage. For example, a discontinuity in the second time period 1004 of a temperature response signal 1000 during a compression-dominated time regime for image pixels 714 of the airfoil surface 102 substantially directly above an internal passageway 110, 120 can be characteristic of a blockage or constriction of that passageway 110, 120.

Thermographic signal reconstruction (TSR) operates on a reconstructed representation of the entire temperature-time history of acquired thermographic data rather than the raw thermographic data. This approach is beneficial because:

A. The reconstructed representation of the temperature-time history of the thermographic data is typically an order of magnitude smaller than the raw thermographic data in terms of the amount of computer memory it requires for storage.

B. The reconstructed representation of the thermographic data is almost entirely free of temporal noise (typically introduced from the infrared camera) and mechanical instability.

C. The reconstructed representation of the thermographic data can be based on an analysis of derivatives (rather than contrast relative to nearby points) of the time evolution of each point in the image 712. Analyzing derivatives lends itself to directly automating the image inspection task because they can be objectively analyzed for characteristic features (zero crossings, extrema, etc.) without visual confirmation by an operator.

D. The inspection requires no a priori knowledge of the physical characteristics of the sample. A priori knowledge is not necessary because the nature of the reconstructed representation of the thermographic image 712 (taken from defect free samples) differs only in scale from sample to sample (there is no deviation in shape from sample to sample).

E. The inspection can be based on a well-known physical model that allows analysis of a sample response to excitation as a deterministic phenomenon and not a phenomenon which is linked to thermographic data collected from neighboring points.

Figure 20:
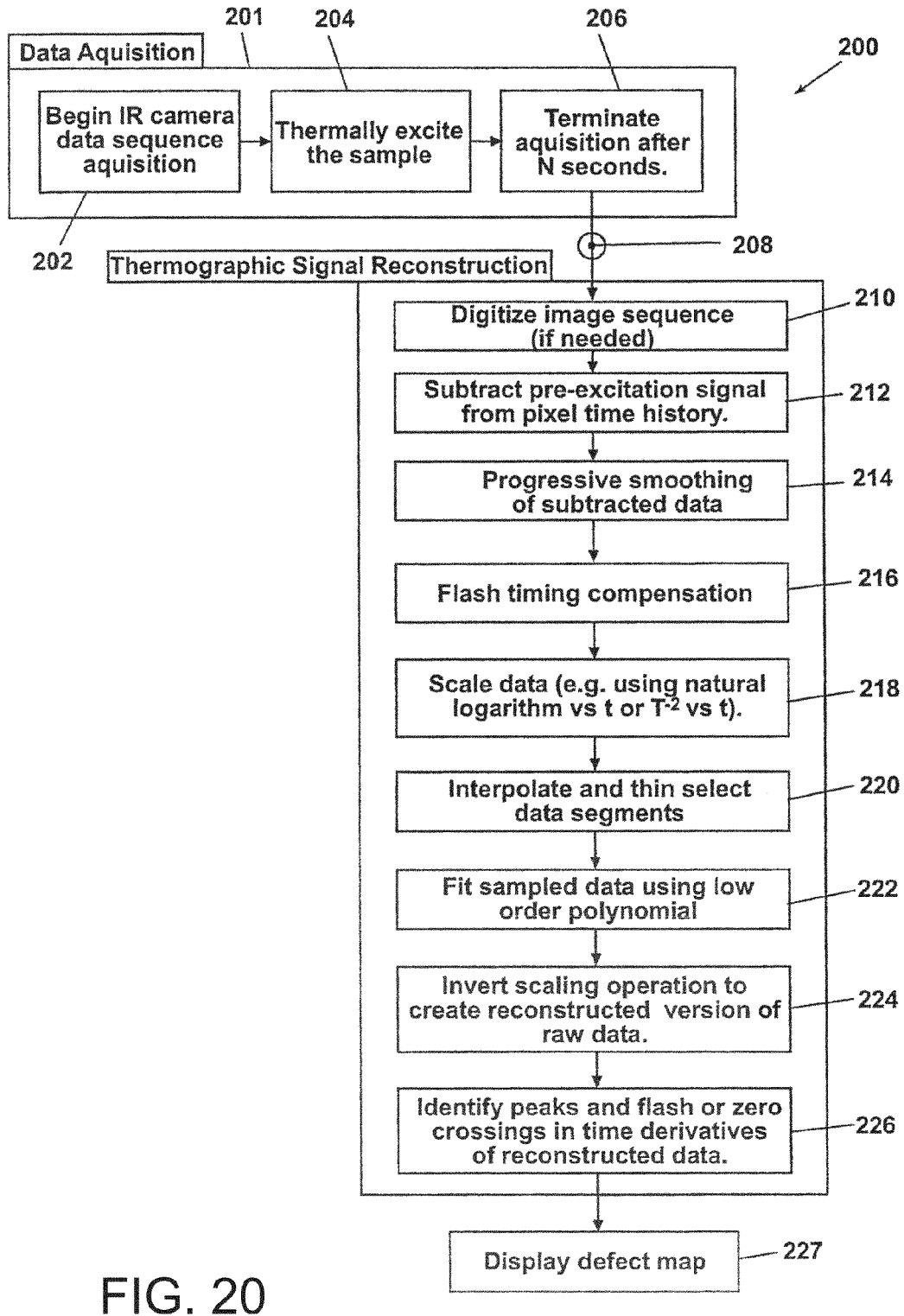
FIG. 20 provides an exemplary arrangement of operations for thermographic signal reconstruction (TSR).

Referring to FIG. 20, a method 200 of thermographic signal reconstruction first involves starting 202 acquisition of a sequence of infrared images 712 from the sample and then thermally exciting 204 the sample (e.g., by introducing a compressed air pulse into an internal channel of the sample). The image sequence can be stored in computer memory, videotape, or any other electronic storage means. The acquisition process is terminated 206 after a predetermined time and digital data corresponding to the image sequence is transferred 208 to a computing device 720 or dedicated hardware for mathematical analysis.

If the data is in analog format, the method includes digitizing 210 the data. The length of the image sequence will depend on the type of material being inspected and the thickness of the component. If the material has low thermal conductivity and/or if the component is relatively this, the image sequence may be lengthened. A typical image sequence from an infrared camera 710 operating at 60 frames per second will contain several hundred frames. In extreme cases, the image sequence may contain as many as several thousands of frames. The time over which the data acquisition step 201 takes place can range over several seconds as the sample temperature returns to equilibrium, but the specific length of time will vary depending on the thermal properties of the sample. Further, the output image sequence (or defect map sequence) can be generated over any time duration bounded between the heating flash event and the last image sequence acquisition event, independent of the sampling rate of the infrared camera 710.

The method includes subtracting 212 the pre-excitation temperature amplitude of each pixel 714 from the post-excitation history temperature for that pixel 714. The process is applied to every pixel 714 in the field of view of every image 712 in the image sequence. The result of subtracting the pre-excitation temperature is that the resulting signal indicates the sample's response to the thermal excitation event and negates any influence that the sample's ambient temperature prior to excitation might otherwise have on the data.

The method may optionally include smoothing 214 the subtracted data using any number of smoothing techniques. Smoothing is necessary because although the overall trend of the surface temperature of the sample is monotonically decreasing, consecutive data points in the post-excitation time history may not behave as expected due to undesirable noise artifacts. These undesirable noise artifacts typically are composed of high frequency components and are easily removed by fitting a straight line segment (or second order polynomial) to groups of adjacent points and replacing a particular point with the value on the straight line. This process can be repeated for every point in the time history; however, the number of points chosen in each grouping should increase as the latter occurring data is smoothed. This allows each line segment to become longer as later points occurring later in the time history are smoothed. This approach accurately models the later occurring data primarily because as time extends further away from the onset of the thermal pulse, the image data tends to change less than it did earlier in time and accordingly behaves more linear.

The method may include executing 216 flash timing compensation. This may be necessary because the one-dimensional heat flow model used as a theoretical basis in this application, assumes that the sample is heated instantaneously by a heat pulse which is infinitesimal, and that this heat pulse occurs at time=$t_o$. In practice, the duration of the heat pulse is finite, and may occur between video frames. The result is a deviation from linearity in the earliest data points in the post-flash time history. By subtracting a time increment from every pixel 714 that is equivalent to the time delay difference between t=0 and the peak of the excitation signal, the early non-linearity is removed. This technique amounts to synchronizing the frame of the camera with the flash event of the heat pulse. If this non-linearity is not compensated for, it manifests itself in a "kink" in the graphical representation of the early segment of the data.

Figure 21A:
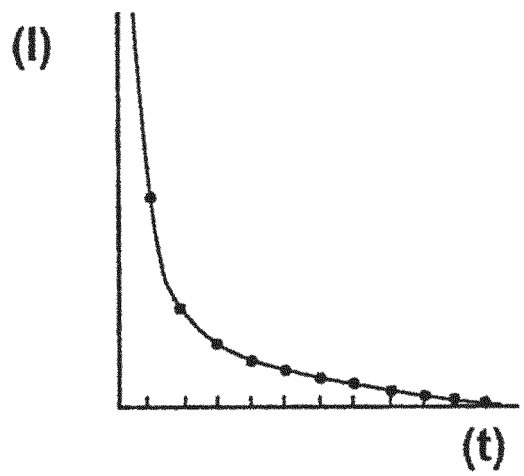
FIGS. 21A and 21B are thermal decay graphs illustrating a temperature-time decay characteristic of an imaged sample in a linear domain (FIG. 21A) and in a logarithmic domain (FIG. 21B).
Figure 21B:
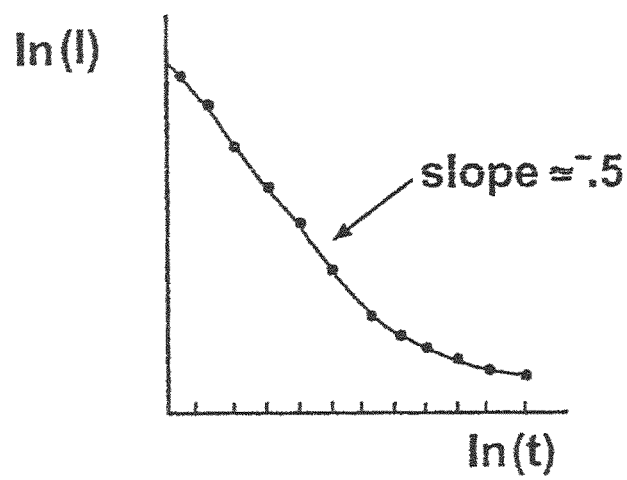

The method further includes scaling 218 the data. The data may be scaled in a way which reduces the dynamic range of the post-flash time history and causes it to behave in a linear, or near linear, manner if no sub-surface defects are present. One such scaling operation entails using the natural logarithm of the temperature versus natural logarithm of time plot (see FIG. 21A of prescaled data and FIG. 21B of post scaled data). This approach results in a temperature versus time plot of a defect free sample as a straight line with a slope of −0.5 (the slope is the same irrespective of the sample composition or hardware used in the imaging process). However, other scaling operations are possible. For example, scaling by using the inverse square of the temperature ($T^{-2}$) versus time results in an ascending straight-line result for a defect-free sample. In either case, the behavior follows the predictions of a one-dimensional solution of the heat diffusion equation.

The method includes interpolating 220 data. The post-excitation response of the sample is governed by diffusion of heat into the sample and this diffusion of heat can be described by a diffusion equation. As a result, the surface temperature changes rapidly immediately after excitation, but the rate of change decreases as time progresses (see FIG. 21A). If data is acquired at a constant (frame) rate, the abrupt decay occurring in the early stages of the sample cool down causes there to be too few early time data points and an excessive number of later data points (this is clearly seen in the plot of temperature decay versus time of FIG. 21A). A more accurate way to model the true thermal behavior of the sample is to add reconstructed points by interpolation between early raw data points in order to increase the influences of early behavior in the fit. Also, improved fidelity to the underlying data is achieved if latter data points are sampled in a way which reduces the influence of the latter occurring data points (typically this is accomplished by thinning later occurring data points).

The method may include fitting 222 the data generated in the interpolating step 220 using a low order polynomial (preferably sixth order or less) using a least squares fit technique. Note that the disclosed method fits a polynomial to the natural logarithm of the temperature-time data and not to the actual (raw) temperature-time data in the linear domain. The low order polynomial serves as a low pass filter to ensure that only the information content of the data representing the thermal response of the sample is preserved and that the noise content of the data is rejected. The use of as low order polynomial as possible is counter intuitive but nonetheless it is the preferred method. Generally speaking, a higher order polynomial will allow you to fit the data with less error. However, because the source of the data is a thermal event (which are low frequency events), any high frequency information contained in the data can be confidently dismissed as noise and such high frequency noise can be easily filtered out using the lowest order polynomial which still permits reasonable fidelity to the underlying thermal information contained in the data. The resulting function for the amplitude for a given pixel at location i, j (i=row, j=column) is defined as:

$$\ln[I_{ij}(t)] = a_0 + a_1 \ln(t) + a_2 [\ln(t)]^2 + \ldots + a_n [\ln(t)]^n \quad (2)$$

The method includes inverted scaling 224 of the data to create a reconstructed version of the new data. Specifically, the inverse of the operation used in scaling step 218 to scale the data can be performed on the polynomial representation of the time history created in the fitting step 222. Accordingly, if we scaled the data using natural log scaling, we would invert the process by operating on the data using the following formula:

$$\begin{aligned} I_{ij}(t) &= \exp\{\ln([I_{ij}(t)])\} \\ &= \exp\{[a_0 + a_1 \ln(t) + a_2 [\ln(t)]^2 + \ldots + a_n [\ln(t)]^n\} \end{aligned} \quad (3)$$

Likewise if we scaled the data using the $T^{-2}$ operation, we conduct an inverse operation to invert the $T^{-2}$ operation.

As can be seen from equation 1, the polynomial resulting from fitting step 222 is a continuous function obtained from the discrete data, and thereby allows the method of the present invention to generate pixel amplitude values for all time values (even for time values that fall between frame acquisitions). Once the polynomial has been generated in fitting step 222 for each pixel 714, each pixel 714 is represented by an array of n polynomial coefficients, which will typically be six coefficients or less making it unnecessary to thereafter store the actual data sequence which can be several hundreds or even several thousands of frames generated by the infrared camera. Because of the polynomial representation includes only an array of coefficients, and because the polynomial representation of the pixel temperature-time characteristic is independent of the length of the data sequence, the amount of data that must be stored for any given pixel 714 is tremendously reduced by the polynomial representation and accordingly, much simpler to manipulate mathematically than raw camera data. The resulting file size for storing the pixel data is independent of the number of images 712 taken by the camera 710, further reducing the memory needed to store or manipulate the image data. For example, in one embodiment, the file size is equal to the number of pixels 714 being imaged multiplied by the number of coefficients in the polynomial multiplied by the number of bytes per coefficient, regardless of the number of images 712. The result of transforming the polynomial function from the logarithmic domain back to the linear domain, is a reconstructed temperature-time curve that has a significantly higher signal-to-noise ratio than the original raw signal, making it more suitable for signal analysis.

Figure 22A:
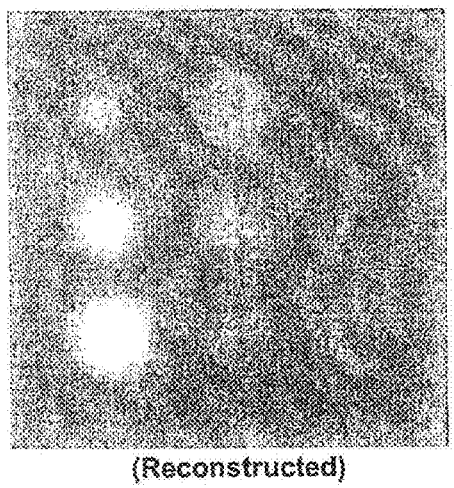
FIG. 22A is an image (formed from reconstructed data) of a front view of a control sample, wherein the control sample contains a plurality of flat bottom holes drilled from the back of the sample at various depths.

The method also includes determining 226 if any subsurface defects are present in the reconstructed data. This determination can be done in any number of ways. Firstly, the reconstructed data for each pixel 714 can be assembled into an image which is displayed graphically to a user. Such an image is known as a defect map and an example is depicted in FIG. 22A. FIG. 22A is a front view of a control sample which has a plurality of flat bottom holes drilled into the sample from the back side. The holes are drilled at various depths (none of which pass through the sample) and accordingly manifest themselves in a reconstructed image as circular elements of various light intensities. These bright spots are also called "hot spots".

Figure 22B:
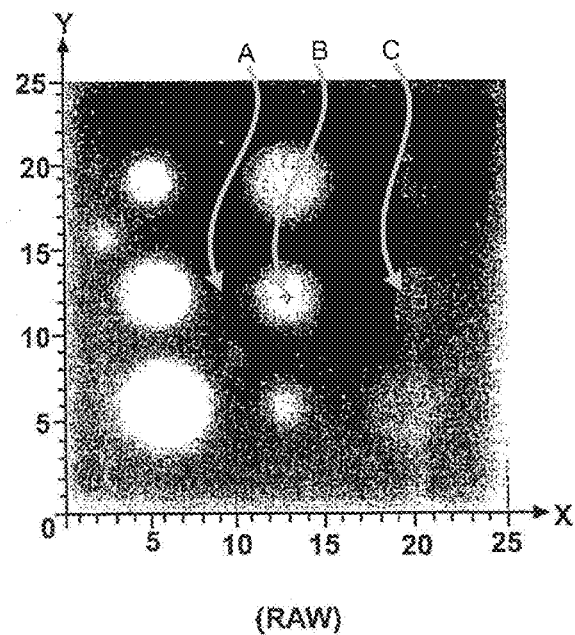
FIG. 22B is an image (formed from raw data, i.e. data that has not been conditioned using the reconstruction techniques of the present invention) of a front view of a control sample
Figure 22C:
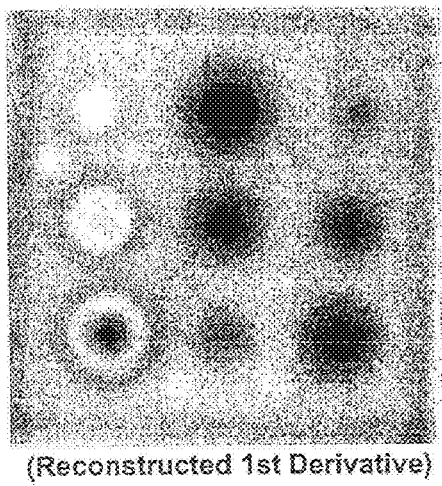
FIGS. 22C and 22D are images created by respectively taking the first and second derivative of the reconstructed data used to form the image of FIG. 22A.
Figure 22D:
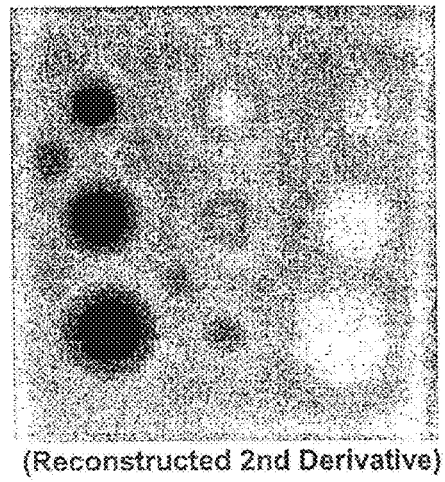
Figure 23:
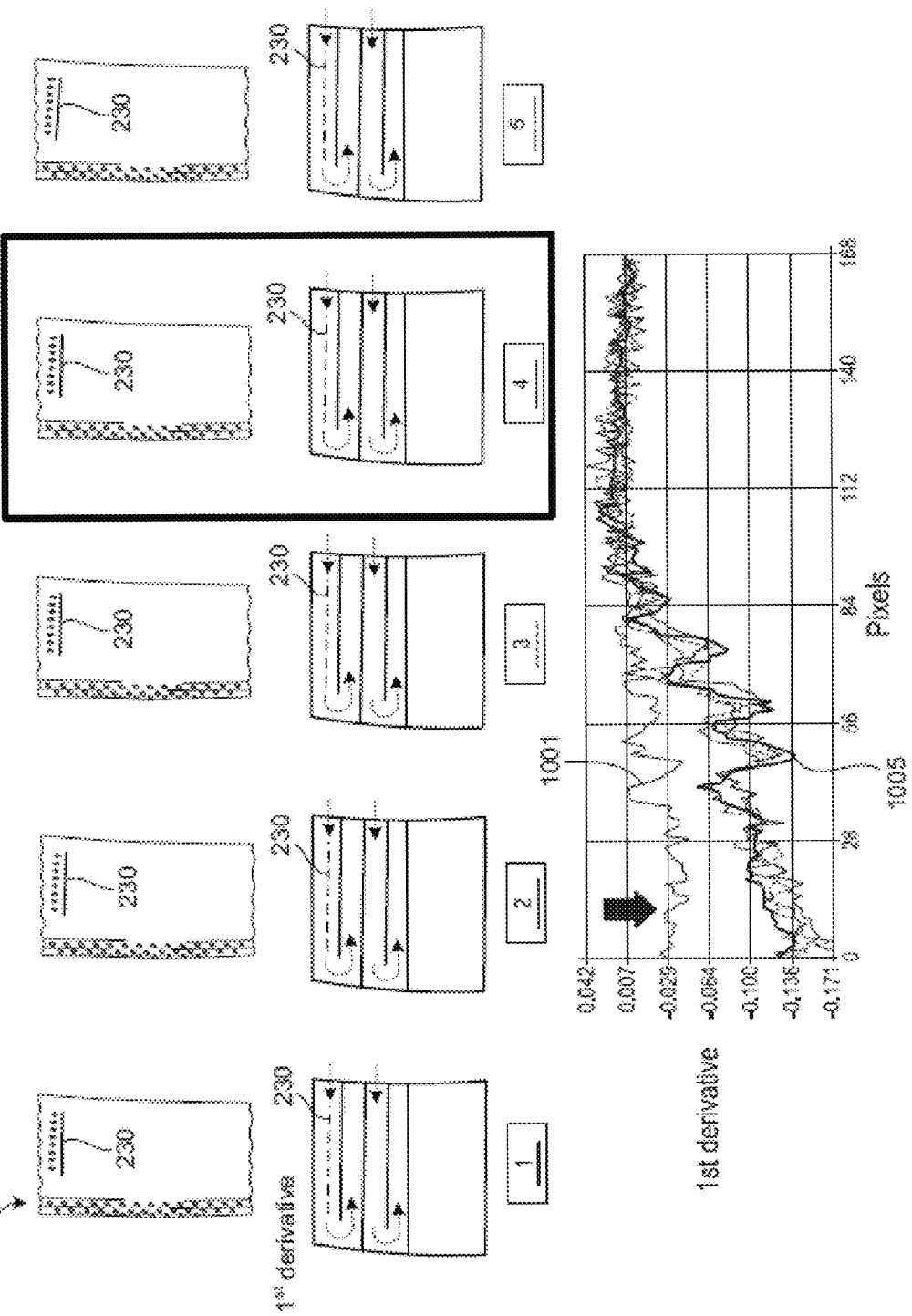
FIG. 23 provides a combined schematic-graphical view of detecting internal passageway debris of an object using path segments applied to a thermal image of the object.
Figure 24:
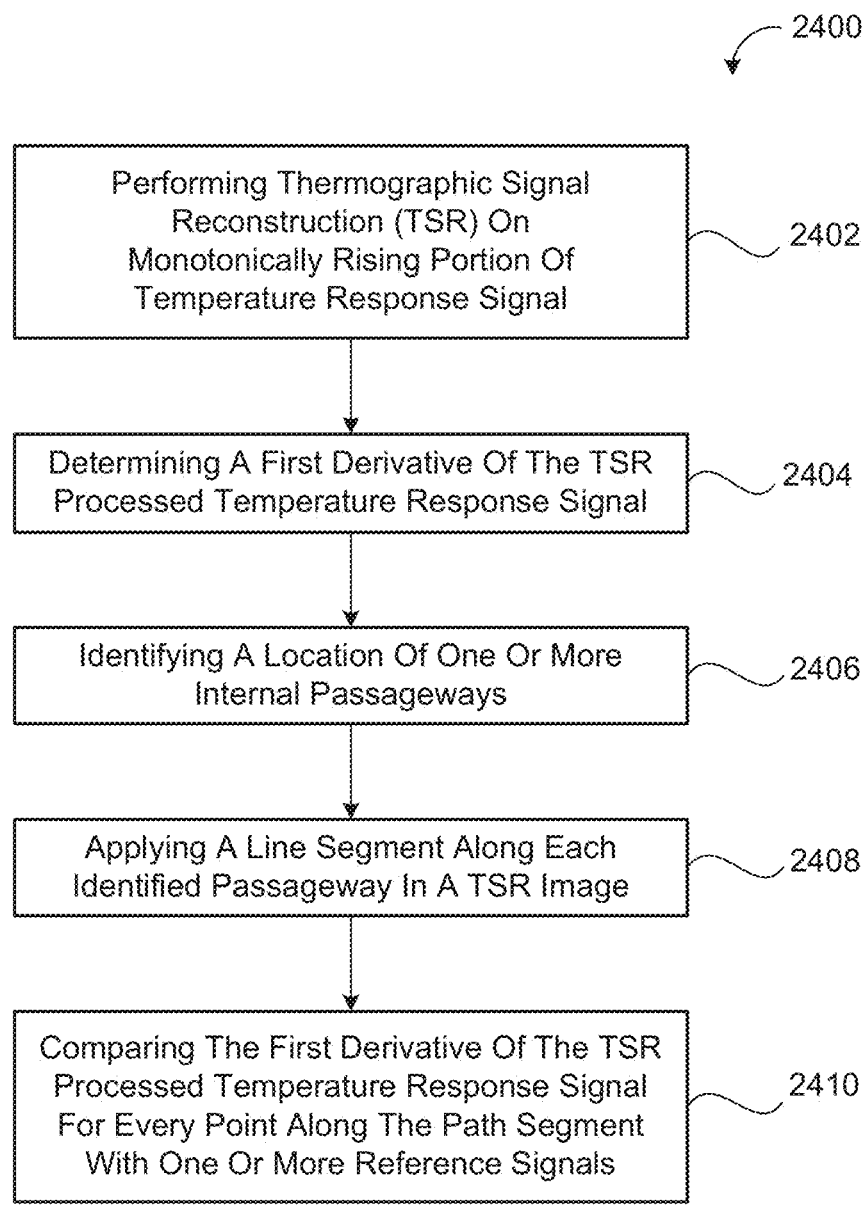
FIG. 24 provides an exemplary arrangement of operations for detecting internal passageway debris of an object.

FIG. 22B is a depiction of the same sample shown in FIG. 22A; however, the depiction in FIG. 22B is constructed from raw thermographic image data wherein the image of FIG. 22A is assembled using reconstructed thermographic image data derived from the process described in FIG. 20. Rather than simply visually analyzing the reconstructed data, in some applications it is far more convenient to examine the first, second, and even third time derivatives of the reconstructed data.

More particularly, if the reconstructed data is represented as:

$$f(t) = \exp\left[\sum a_1 \left[\ln(t)\right]_{i=0}^{N}\right]^i \quad (4)$$

the first derivative can be expressed as:

$$f'(t) = t^{-1}[\Sigma i a_i[\ln(t)]^{i-1}]f(t) \quad (5)$$

and the second derivative can be expressed as:

$$f''(t) = t^{-1}[\Sigma i a_1[\ln(t)]^{i-1}]^2 f(t) + t^{-2}\{[\Sigma i(i-1)a_i[\ln(t)]^{i-2}] - [ia_i[\ln(t)]^{i-1}]\}f(t) \quad (6)$$

Images of the first and second derivatives (and other higher order derivatives) can be generated from Equations 5 and 6 through any means, if desired, by entering time information into the polynomial or its derivatives. Note that because the derivatives of the image data are calculated analytically rather than by fitting a straight line to the tangent of the noisy image data, the results obtained from the calculated derivatives yields more accurate results than attempts to compute the average over many noisy data points. Further, analytical calculation of the derivatives yields results that are true instantaneous derivatives rather than differentials over an interval spanning several image frames.

Also note that it is not necessary to convert the expressions back to their graphical format in order to glean useful information therefrom, it is sufficient to isolate and manipulate the arguments from expressions (4) and (5) to yield valuable information.

Because the method focuses on differentiating and analyzing the polynomial function instead of the raw image data, obtaining information about the thermal characteristics of the sample is much simpler because differentiating the polynomial representation is less computationally complex than differentiating a noisy signal. More particularly, operating on the coefficients of the polynomial, and not on the original data, eliminates the need to manipulate hundreds or even thousands of separate images, greatly improving the speed in which the image data can be analyzed. Also, because the first and second derivatives are obtained by manipulating the polynomial expression rather than conducting linear regression or curve fitting, the derivatives do not themselves contribute any noise to the final result. Further, because the method uses noise-reduced, analytically differentiated data obtained from scaled data, the noise reduction provided by the method allows more accurate detection of deeper and weaker defects as well as large defects encompassing the entire field of view.

Once steps 201 through 226 have been conducted for every pixel 714 at a given time t, an image representation 227 of the behavior of the sample at that time can be scaled to match the dynamic range of the display device. This scaling operation can be conducting using any common statistical scaling algorithm.

The image 227 or images based on the polynomial and/or its derivatives can be displayed on an output device, such as on a computer display screen. The display screen can be one or more discrete points on the sample, a single reconstructed image at a selected time t (FIG. 22A) or a sequence of reconstructed images displayed as a movie (not shown). The temporal resolution of the movie can be different than the actual data acquisition frame rate, if desired, to show the changes in the sample temperature more clearly; this can be conducted easily because the derived polynomial is a continuous function, as noted above.

Referring again to FIGS. 18A, 18B, 23 and 24, in some implementations, a method 2400 of detecting partial or relatively small blockages (e.g., core residue forming a coating along the passageway wall 114, 124) includes performing 2402 the TSR process on the monotonically rising portion 1020 of the temperature response signal 1000 for every pixel 714 during a time interval starting with the onset of air compression within the airfoil 100 and ending at a time when the corresponding pixel 714 attains its maximum temperature. The method includes determining 2404 a first derivative 1001 or second derivative of the TSR processed temperature response signal 1000 and identifying 2406 a location of one or more internal passageways 110, 120. The method further includes applying 2408 a line segment 230 along each identified passageway in a TSR image 227 and comparing 2410 the first derivative 1001 or the second derivative of the TSR processed temperature response signal 1000 at a particular time, or the maximum value of the derivative, for every point along the path segment 230 with one or more reference signals 1005 (e.g., first derivative 1001 of the TSR processed temperature response signal 1000 for reference airfoils 100 or components having verified unblocked passageways 110, 120 and exit holes 122). Since temperature response signals 1000 derived from corresponding pixels 714 of a series of thermal images iteratively captured from the infrared camera 710 at a specified frame rate can provide a time history of temperature change along an imaged airfoil surface 102 due to a received compressed air pulse, the process can be used to verify placement, size, arrangement, and/or level of blockage of internal structures (e.g., internal passageways 110, 120) of the airfoil 100.

The first or second derivative along a line segment 230 taken at a time (e.g., an optimal time) of a known clear (no residual core) component can be stored as a reference. Subsequent test components can be statistically correlated to the reference and automatically rejected if a correlation between the tested component and the reference component falls outside a set limit or range. A set of line segment locations and time settings for a particular airfoil 100 can be stored and recovered at a later time so that the identical test can be performed automatically on subsequent air foils 100 (e.g., of the same type). Instead of or in addition to comparing line segments 230, the entire derivative image of the airfoil 100 at the specified time can be compared to the reference.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

Now referring to FIGS. 1-7, as previously described, a thermographic method for evaluating a component such as an airfoil 100 (e.g., a turbine blade or a vane) based on rapid compression of air in the passageways 110, 120 of the airfoil 100 to create an internal heat pulse. In some examples, the airfoil 100 contains static air, and may be in a thermal equilibrium state with its environment. In other examples, the airfoil 100 has static air and is rapidly exposed to a vacuum removing all the air from the passageways 110, 120. Therefore, the air disturbance can be caused by either compressing the static air located in the internal passageway 110, 120 of the airfoil 100 or decompressing the static air. In situations where the airfoil 100 contains static air, once the passageway 110, 120 is subjected to an air pulse, some of the heated air in the airfoil 100 is expelled through holes 122 in connection with the passageway 110, 120 of the airfoil 100. The air in the airfoil 100 is compressively heated due to the substantially instantaneous compression of the static air present in the passageways 110, 120, causing the air to heat. The compressive heating compresses the air in the passageway 110, 120 and causes the temperature to increase in the internal surfaces of the inlet and exit passageways 110, 120. The compressive heating is used to assess the state of the cooling passages in communication with the holes 122. In addition, some of the remaining heated air residing within the airfoil 100 heats the internal passageway walls 114, 124 of at least some internal passageways 110, 120. The internal walls 114, 124 may consequently conduct heat from the internal passageways 110, 120 though the airfoil wall 104 to the exterior surface 102 of the airfoil 100. This phenomena is used to assess the condition of the wall, e.g. either its thickness or thermal diffusivity (if one is known, the other may be calculated), or to detect the presence of foreign material (blockages or abnormalities) that may resides on the internal wall, e.g. residual ceramic core from the casting process. This heating of the passage wall is conducted through the airfoil 100 (e.g., turbine blade) material and manifests itself on an external surface 102 (i.e., viewable) of the airfoil 100. Therefore, the process of compressively heating the air causes thermal diffusion through the airfoil wall 104, and ultimately, a temperature rise at the exterior surface 102 of the airfoil 100 allows determination of changes in airfoil wall thickness T. In examples where the airfoil 100 comprises a homogeneous superalloy structure, thermal diffusivity may be relatively constant throughout the airfoil 100. Moreover, changes in a propagation time for heat to diffuse through the airfoil wall 104 and/or a maximum amplitude of the airfoil surface temperature may be associated with changes in airfoil wall thickness T along the airfoil 100.

Referring to FIGS. 22A-22D, in some implementations, and as previously discussed, the thermographic detection may include determining if any sub-surface defects are present in the reconstructed data for each pixel. In some examples, the reconstructed data for each pixel 714 can be assembled into an image which may be displayed graphically to a user and shown in FIG. 22A. FIG. 22B is a depiction of the same sample shown in FIG. 22A; however, the depiction in FIG. 22B is constructed from raw thermographic image data wherein the image of FIG. 22A is assembled using reconstructed thermographic image data derived from the following process.

In some implementations, the thermographic signal detected by the infrared camera may be small and noisy (i.e., small signal-to-noise ratio). To facilitate more accurate measurement of this signal, as well as additional mathematical operations, it is highly desirable to fit the data to a model or prescribed function and perform subsequent measurement operations on the model or function. This type of approach is explained more fully in U.S. Pat. No. 7,724,925 (and as previously stated, is hereby incorporated by reference in its entirety). This approach is coined Thermographic Signal Reconstruction (or "TSR") in the '925 patent. However, the TSR approach as well as previous model-based schemes for processing thermographic data, are typically based on simplifying assumptions that do not adequately account for the complexities of an airfoil 100 such as a turbine blade. For example, after the transient compression pulse (which compressively heats the internal passage walls 114, 124), air flows through the airfoil 100 in a steady state, acting to cool the airfoil 100. When inspecting a turbine blade, the precise nature of the cooling is complex due to the presence of pedestals, turbulators and other structures designed to direct the flow of fluid in the blade during normal operation. Furthermore, the thickness of the turbine blade wall may change significantly over a short distance. The net result is that a simple 1-dimensional modeling of heat flow from the internal to external wall may not accurately fit the experimental data of a turbine blade or any airfoil having varying wall thicknesses. While 2-dimensional modeling based on exact specification of the blade is possible, given the complexity of modern turbine blade design, such an approach would be extremely cumbersome in a production environment.

Therefore, to achieve the fitting of the detected signal, we consider the three events that occur as a result of the compressive heating occurring in an airfoil 100. The events are:
1. Compressive heating: the turn-on of the pulse causes rapid compression heating of the air already in the blade.
2. Steady state air flow: after the static air has been expelled from the blade, steady state airflow follows.
3. Rapid expansion cooling: the turn-off of the pulse causes rapid expansion cooling of the steady state airflow in the blade.

In some implementations, rather than implementing a model that describes the three events that occur due to the compressive heating process, we can consider each event independently and view the process as the sum of 3 independent 1-dimensional functions.

First, the compressive heating event is considered. The external surface temperature due to internal turn-on and off of pulses are represented by the positive and negative polarity 1 dimensional expression for instantaneous heating of a surface 102 of a slab with thickness T and thermal diffusivity α, and where time is measured from the initiation of the turn-on pulse.

$$T_{emp} = \frac{1}{T}\left(1 + 2\sum_{n=1}^{\infty} e^{\alpha n^2 \pi^2 t/L^2} \cos(n\pi)\right) \quad (7)$$

Figure 25A:
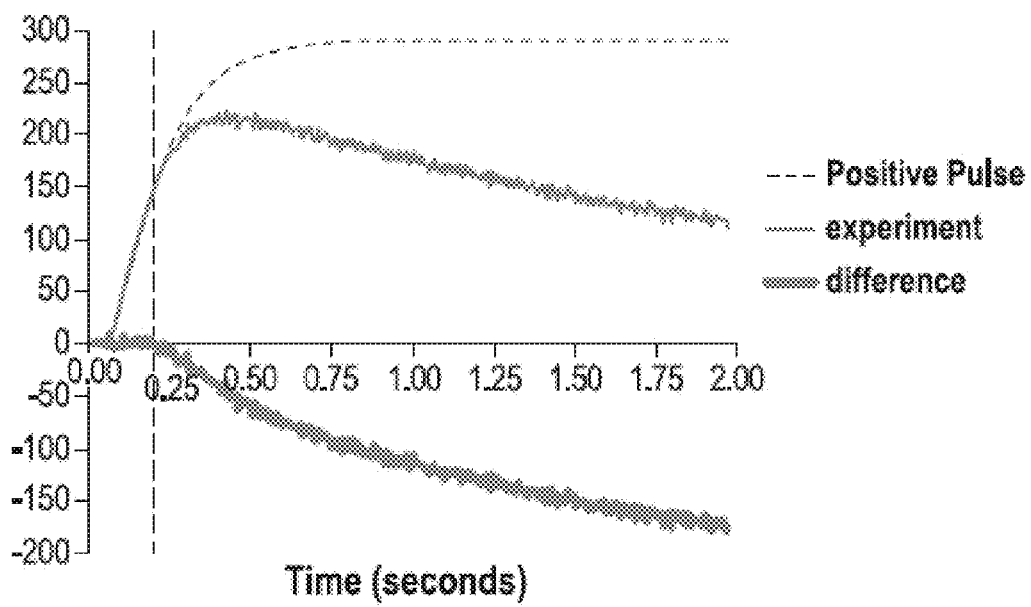
FIG. 25A provides a comparison graph of experimental and theoretical exterior surface temperature on an airfoil.

A comparison of the compression (positive) pulse model in Eq. 7 and actual response for 2 seconds of airflow are shown in FIG. 25A. The results from the equation and the actual experimental results are similar during the initial heating phase (to the left of the dashed vertical line). However, subsequent experimental data cools gradually due to steady state cooling.

Figure 25B:
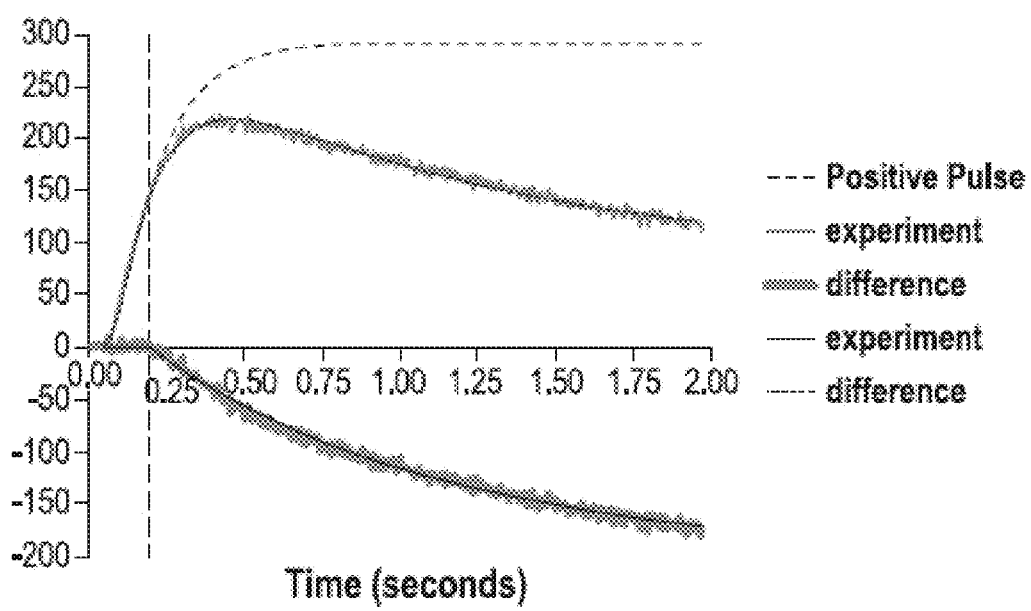
FIG. 25B provides a graph of the approximation of cooling of the exterior surface due to steady state airflow by an exponential decay function.

Second, referring to FIG. 25B, the steady state air flow is considered. The difference between the experimental and theoretical data during this steady state period can be approximated by an exponential decay function. The sum of the positive pulse and the exponential decay function comprise a reasonable approximation to the onset and steady state behavior of the signal.

Figure 25C:
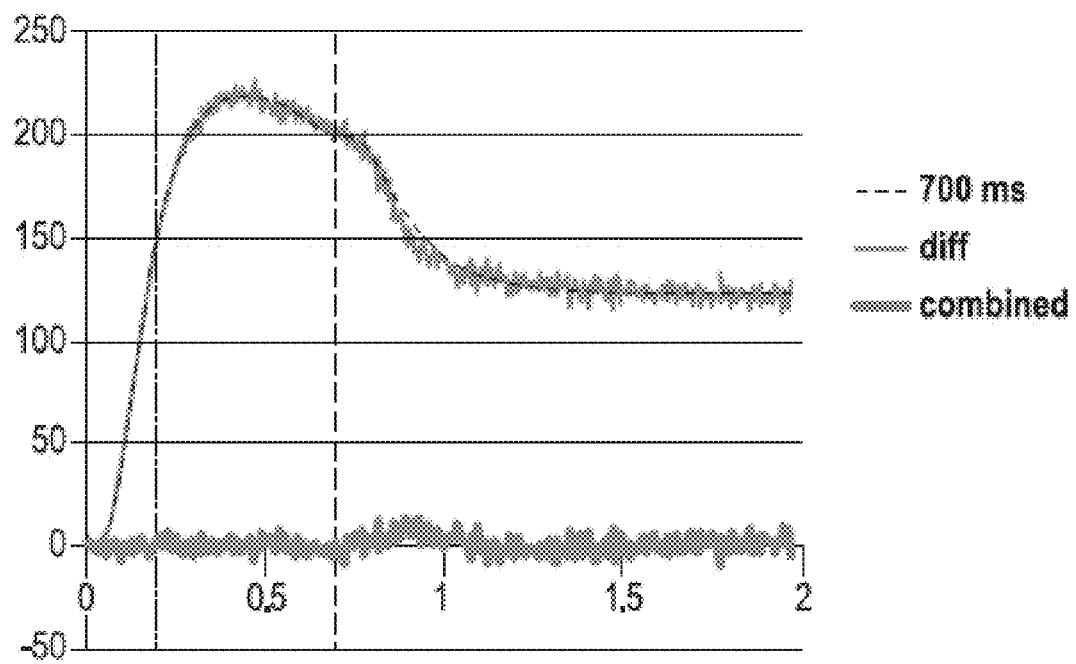
FIG. 25C provides a graph of the approximation of cooling of the exterior surface due to the shut-off of the airflow pulse.

Third, referring to FIG. 25C, the rapid expansion cooling is considered. due to the airfoil 100 response to the airflow shut-off—The turn-off of the pulse cause rapid expansion cooling of the steady state airflow in the blade.

Figure 25D:
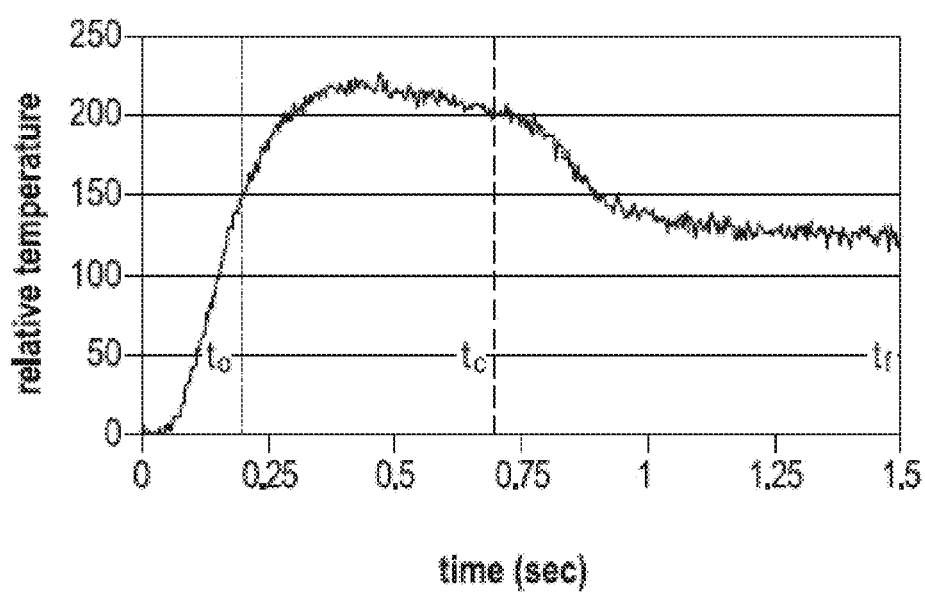
FIG. 25D provides a graph of the piecewise expression of the airflow during turn-on of the pulse through the turn-off of the pulse.

Referring to FIG. 25D the three events discussed are used to model the pulsed airflow inspection method for creating a noise-free replica of each pixel time history. An early section of the data, $0<t<t_o$, is taken to represent pure 1-dimensional heat flow and the parameters of the 1-dimensional through transmission series solution which are optimized to fit the data.

$$T_{temp-ON} = \frac{1}{T}\left(1 + 2\sum_{n=1}^{\infty} e^{\alpha n^2 \pi^2 t/L^2} \cos(n\pi)\right) \quad (8)$$

Next the remaining duration until the time the valve is expected to close, $t_o<t<t_c$, is modeled using an exponential decay function:

$$E(t)=Ae^{-B(t-t_0)}+C \quad (9)$$

The three undetermined parameters A, B and C are optimized to fit the data in this section using a least squares fit. This term is added to the positive pulse model to represent the steady state airflow cooling and lateral heat flow cooling of the surface (the data shown in FIG. 25D was taken from a hot spot in the imaged region).

In the final section of the data set, $t_c<t<t_f$, the data are modeled by holding the steady state term constant at its value at $t_c$, continuing the positive pulse term and adding a negative pulse term, N(t) that originates at $t_c$. The negative pulse material property parameters are taken to be the same as those for the positive pulse but the magnitude of the pulse is optimized to fit the data.

The final piecewise defined expression is:

$$\begin{aligned} T(t) &= P(t), & 0 < t < t_o \\ T(t) &= P(t) + E(t_c), & t_o < t < t_c \\ T(t) &= P(t) + E(t_c) + N(t-t_c), & t_c < t < t_f \end{aligned} \quad (10)$$

The method described above is used to create a noise-free expression of each pixel time history that is more accurate and precise than the raw data acquired from the original noisy data collected by the IR camera. The expression or the derivative (or other attribute) of the expression may then be used to generate attribute maps, such as maximum (or minimum) amplitude of each time history, time of occurrence of maximum (or minimum) amplitude, or time at which half-maximum amplitude occurs. These attributes may then be used to calculate thermophysical properties, e.g. thermal diffusivity or thickness, using well-known formulae for 1-dimensional heat flow through a solid slab.

In some implementations, it is desirable to inspect the airfoil 100 at different times during its lifetime to track its performance and its condition after exposure to its operating environment, where it will be exposed to thermal shock, high temperature and high stress. Therefore, the method described may be used to track the condition of the airfoil 100 over its lifetime (i.e., before, during, and after the airfoil 100 is used for its intended purpose), since either a reduction in wall thickness or accumulation of material on the interior walls 114, 124 will cause corresponding changes in the attribute map. It is contemplates that a history of thermal signatures (i.e., attribute image) can be stores (e.g., one thermal signature is collected after each approximately N hours of actual component use). This history of N signatures can be analyzed to determine the presence of obstructions, changes, etc. An attribute image could encompass blade thickness, blade diffusivity, half-rise time, etc. The attributes calculated from the expression derivatives are invariant with respect to the amplitude of the energy input or the surface 102 characteristics of the blade (these parameters affect signal amplitude, but not signal shape, which is retained by the derivative). Therefore, allowing the tracking of the condition of the airfoils 100 over its lifetime. Changes in wall thickness or accumulation of material on the interior walls will cause corresponding changes in the attribute map. The map may be an image of the blade or blade section, or a collection of attributes along a line (or lines) corresponding to internal passageways 110, 120 or elsewhere on the blade, indicating whether the blade cooling performance has changed since the original evaluation. Thus collecting data over the functional lifetime of an airfoil 100 provides information for improving the airfoil 100. In some examples, the collected maps are stored on a storing device and may be compared at different time intervals to track the changes of the airfoil 100 over time While this specification contains many specifics, these should not be construed as limitations on the scope of the invention or of what may be claimed, but rather as descriptions of features specific to particular implementations of the invention. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A method of thermal inspection of a component defining at least one internal passageway, the internal passageway attaining a thermal equilibrium state with its surrounding environment, the method comprising:
   capturing a sequence of a rapid increase in thermal indications over a short period of time of a surface of the component;
   compressively heating the at least one internal passageway by way of delivering an airflow disturbance into the at least one internal passageway, wherein said airflow disturbance is initially at thermal equilibrium with the internal passageway;
receiving a temperature response signal as a function of time based on the received thermal indications; and
determining a level of blockage of the at least one internal passageway based on the temperature response signal.

2. The method of claim 1, further comprising:
receiving a thermal diffusivity of the component;
fitting a mathematical expression to the received temperature response signal; and
determining a wall thickness of the component.

3. The method of claim 1, further comprising:
executing thermographic signal reconstruction on a monotonically rising portion of the temperature response signal occurring during a time interval starting at an onset of the air disturbance delivery and ending at a time when the temperature response signal attains a maximum temperature; and
comparing at least one of a first derivative of the reconstructed temperature response signal with a corresponding first derivative of a reconstructed reference temperature response signal and a second derivative of the reconstructed temperature response signal with a corresponding second derivative of the reconstructed reference temperature response signal to determine if the component meets a specification.

4. The method of claim 1, wherein delivering an airflow disturbance further comprises
expelling a film of air across a surface of the component.

5. The method of claim 4, further comprising:
determining a shape of the air film based on at least one representation; and
comparing the determined air film shape to a reference shape to determine whether the exit hole meets a specification.

6. The method of claim 1, further comprising:
identifying a monotonically rising portion of the temperature response signal occurring during a time interval starting at an onset of the air disturbance delivery and ending at a time when the temperature response signal attains a maximum temperature; and
identifying a monotonically falling portion of the temperature response signal occurring during a time interval starting at cessation of the air disturbance delivery and ending at a time when the temperature response signal reaches a minimum temperature.

7. The method of claim 1, further comprising:
determining a first derivative of the temperature response signal; and
determining the level of blockage of the at least one internal passageway based on the first derivative of the temperature response signal.

8. A method of thermal inspection of a component defining at least one internal passageway, the internal passageway attaining a thermal equilibrium state with its surrounding environment, the method comprising:
capturing a sequence of thermal indications of a surface of the component;
delivering an airflow disturbance into the at least one internal passageway, wherein said airflow disturbance is initially at thermal equilibrium with the internal passageway;
receiving a temperature response signal as a function of time based on the received thermal indications;
determining a level of blockage of the at least one internal passageway based on the temperature response signal;
capturing a first sequence of thermal indications before the component has been subjected to use as its intended purpose, and
capturing a second sequence of thermal indications after the component has been subjected to use as its intended purpose.

9. The method of claim 8, further comprising
comparing the first and second sequence of thermal indications and determining a level of blockage of the at least one internal passageway based on the compared indications.

10. A method of thermal inspection of a component defining at least one internal passageway, the method comprising:
A) receiving a sequence of a rapid increase in thermal indications over a short period of time of a surface of the component;
B) delivering a fluid disturbance into the at least one internal passageway;
C) compressively heating the at least one internal passageway by way of delivering the fluid disturbance; and
D) receiving a temperature response signal as a function of time based on the received indications caused by the heating of step C.

11. The method of claim 10, wherein the duration of compressively heating the at least one internal passageway is one or more tens of milliseconds.

12. The method of claim 10, further comprising:
identifying a location of the at least one internal passageway based on the sequence of thermal indications; and
applying a line segment along each identified passageway.

13. A method of thermal inspection of a component defining at least one internal passageway, the method comprising:
A) receiving a sequence of thermal indications of a surface of the component;
B) delivering a fluid disturbance into the at least one internal passageway;
C) compressively heating the at least one internal passageway by way of delivering the fluid disturbance; and
D) receiving a temperature response signal as a function of time based on the received indications caused by the heating of step C;
identifying a location of the at least one internal passageway based on the sequence of thermal indications;
applying a line segment along each identified passageway; and
determining a first derivative of the temperature response signal at a particular time for every point along the line segment with one or more reference signals to determine if the component meets a specification.

14. The method of claim 13, further including
verifying one of placement, size, arrangement, and level of blockage of the internal passageway by way of a time history of temperature change of the component.

15. A method of thermal inspection of a component defining at least one internal passageway, the method comprising:
A) receiving a sequence of thermal indications of a surface of the component;
B) delivering a fluid disturbance into the at least one internal passageway;
C) compressively heating the at least one internal passageway by way of delivering the fluid disturbance; and
D) receiving a temperature response signal as a function of time based on the received indications caused by the heating of step C;
capturing a first sequence of thermal indications before the component is subjected to use;

capturing a second sequence of thermal indications after the component is subjected to use; and comparing the first and second set of thermal indications for verifying one of placement, size, arrangement, and level of blockage of the internal passageway.

16. A method of thermal inspection of a component defining at least one internal passageway having static fluid present therein at a thermal equilibrium state with its surrounding environment, the method comprising:

receiving a continuous sequence of a rapid increase in thermal images over a short period of time of at least an exit hole defined by the at least one internal passageway at a surface of the component;

delivering a pressurized airflow disturbance into the at least one internal passageway for expelling the static fluid, the pressurized airflow disturbance disrupting the thermal equilibrium state of the at least one internal passageway by way of compressive heating;

receiving a temperature response signal as a function of time based on the received thermal images of the pressurized airflow disturbance; and delivering a continuous steady flow of pressurized air into the at least one internal passageway.

17. The method of claim 16, further comprising:

executing thermographic signal reconstruction on a monotonically rising portion of the temperature response signal occurring during a time interval starting at an onset of the air disturbance delivery and ending at a time when the temperature response signal attains a maximum temperature; and comparing at least one of a first derivative of the reconstructed temperature response signal with a corresponding first derivative of a reconstructed reference temperature response signal and a second derivative of the reconstructed temperature response signal with a corresponding second derivative of the reconstructed reference temperature response signal to determine if the component meets a specification.

18. The method of claim 16, wherein delivering an airflow disturbance further comprises:

expelling a film of air across a surface of the component;

determining a shape of the air film based on at least one representation; and comparing the determined air film shape to a reference shape to determine whether the exit hole meets a specification.

19. The method of claim 16, further comprising:

identifying a monotonically rising portion of the temperature response signal occurring during a time interval starting at an onset of the air disturbance delivery and ending at a time when the temperature response signal attains a maximum temperature; and identifying a monotonically falling portion of the temperature response signal occurring during a time interval starting at cessation of the air disturbance delivery and ending at a time when the temperature response signal reaches a minimum temperature.

20. A method of thermal inspection of a component defining at least one internal passageway having static fluid present therein at a thermal equilibrium state with its surrounding environment, the method comprising:

receiving a continuous sequence of thermal images of at least an exit hole defined by the at least one internal passageway at a surface of the component;

delivering a pressurized airflow disturbance into the at least one internal passageway for expelling the static fluid, the pressurized airflow disturbance disrupting the thermal equilibrium state of the at least one internal passageway by way of compressive heating;

receiving a temperature response signal as a function of time based on the received thermal images of the pressurized airflow disturbance;

delivering a continuous steady flow of pressurized air into the at least one internal passageway;

receiving a first sequence of thermal images before the component is subjected to use;

receiving a second sequence of thermal images after the component is subjected to use; and comparing the first and second sequences of thermal images for verifying one of the placement, size, arrangement, and level of blockage of the internal passageway.

21. A thermographic testing system comprising:

a pressurized air source configured to direct fluid to a component having at least one internal passageway at a thermal equilibrium state with its surrounding environment;

a thermal indicator arranged to capture a status of the component; and a computing device in communication with the indicator, the computing device:

receiving a sequence of a rapid increase in thermal indications over a short period of time of at least an exit hole defined by the at least one internal passageway at a surface of the component;

compressively heating the at least one internal passageway by causing the air source to deliver a pressurized airflow disturbance at the thermal equilibrium state of the at least one internal passageway into the at least one internal passageway of the component;

determining a temperature response signal as a function of time based on the received indications; and determining a level of blockage of the at least one internal passageway.

22. A thermographic testing system comprising:

a pressurized air source configured to direct fluid to a component having at least one internal passageway at a thermal equilibrium state with its surrounding environment;

a thermal indicator arranged to capture a status of the component; and a computing device in communication with the indicator, the computing device:

receiving a sequence of thermal indications of at least an exit hole defined by the at least one internal passageway at a surface of the component, causing the air source to deliver a pressurized airflow disturbance at the thermal equilibrium state of the at least one internal passageway into the at least one internal passageway of the component, determining a temperature response signal as a function of time based on the received indications, determining a level of blockage of the at least one internal passageway, captures a first sequence of thermal indications before the component is subjected to use, and captures a second sequence of thermal indications after the component is subjected to use; and compares the first and second sequence of thermal indications for verifying one of the placement, size, arrangement, and level of blockage of the internal passageway.

23. The thermographic testing system of claim 22, wherein the computing device:

determines a first derivative of the temperature response signal;

compares the first derivative of the temperature response signal with a first derivative of the temperature response signal of the component determined before exposure of the component to its intended use.

24. The thermographic testing system of claim 23, wherein the computing device
identifies peaks of the first derivative of the temperature response signal to determine the onset time period and the shut-off time period.

25. A method of thermal inspection of a component during a portion of its lifetime, the lifetime having an operational phase and a testing phase, wherein during its operational phase the component is being used for its intended purpose, the component defining at least one internal passageway, the method comprising:
moving the component from the operational phase to a testing phase;
capturing a sequence of thermal indications of a surface of the component; delivering an airflow disturbance into the at least one internal passageway at an initial time t=0; receiving a temperature response signal as a function of time based on the received thermal indication; fitting a first mathematical expression to the received temperature response signal for a duration of time td1 wherein time to<the time td1<time to, fitting a second mathematical expression to the received temperature response signal for a second duration of time td2 wherein the time to<the time td2<time tc where the time tc indicates a shutoff time of the airflow disturbance; returning the component from the testing phase to the operational phase; and comparing the first and second mathematical expressions with another first and second mathematical expressions fitted before moving the component from the operational phase to the testing phase.

26. The method of claim 25, further comprising
fitting a third mathematical expression to the received temperature response signal for a third duration of time $t_3$ wherein the time $t_c$<the time $t_3$<time $t_f$ and the time $t_f$ is a final time of the thermal inspection.

27. The method of claim 26, further comprising
comparing the third mathematical expression with another third mathematical expression fitted before moving the component from the operational phase to the testing phase.

28. The method of claim 25, wherein the first mathematical expression is different from the second mathematical expression.

29. The method of claim 25, wherein the first mathematical expression is:

$$T_{temp-ON} = \frac{1}{T}\left(1 + 2\sum_{n=1}^{\infty} e^{\alpha n^2 \pi^2 t/L^2} \cos(n\pi)\right)$$

wherein $T_{emp-ON}$ is a temperature of the external surface of the component, T is the thickness of the component, and α is the thermal diffusivity of the component.

30. The method of claim 25, wherein the second mathematical expression is:

$$E(t) = Ae^{-B(t-t0))} + C$$

wherein A, B and C are calculated using a least square fit.

31. The method of claim 25, further comprising
generating an attribute map from the first and second mathematical expressions, wherein the attribute map is selected from the group consisting of
a maximum or minimum amplitude of each time history of temperature change of the component,
time of occurrence of the maximum or minimum amplitude,
a time at which a half-maximum occurs, and
a derivative of the first and second mathematical expressions.

32. A thermographic testing system for inspecting a component during a portion of its lifetime, the lifetime having an operational phase and a testing phase, wherein during its operational phase the component is being used for its intended purpose, during the testing phase, the testing system comprising:
an air source configured to direct fluid to a component having at least one internal passageway;
a thermal indicator arranged to capture a status of the component; and
a computing device in communication with the indicator, the computing device:
capturing a sequence of thermal indications of a surface of the component; delivering an airflow disturbance into the at least one internal passageway at an initial time t=0; receiving a temperature response signal as a function of time based on the received thermal indication; fitting a first mathematical expression to the received temperature response signal for a duration of time td1 wherein 0<the time td1 time<to, fitting a second mathematical expression to the received temperature response signal for a second duration of time td2 wherein the time to<the time td2<time tc where the time tc indicates a shutoff time of the airflow disturbance; returning the component from the testing phase to the operational phase; and comparing the first and second mathematical expressions with another first and second mathematical expressions fitted before moving the component from the operational phase to the testing phase.

33. The thermographic testing system of claim 32, wherein the computing device fits a third mathematical expression to the received temperature response signal for a third duration of time $t_3$ wherein the time $t_c$<the time $t_3$<time $t_f$ and the time $t_f$ is a final time of the thermal inspection.

34. The thermographic testing system of claim 32, wherein the computing device compares the third mathematical expression with another third mathematical expression fitted before moving the component from the operational phase to the testing phase.

35. The thermographic testing system of claim 32, wherein the first mathematical expression is different than the second mathematical expression.

36. The thermographic testing system of claim 32, wherein the first mathematical expression is:

$$T_{temp-ON} = \frac{1}{T}\left(1 + 2\sum_{n=1}^{\infty} e^{\alpha n^2 \pi^2 t/L^2} \cos(n\pi)\right)$$

wherein $T_{emp-ON}$ is a temperature of the external surface of the component, T is the thickness of the component, and α is the thermal diffusivity of the component.

37. The thermographic testing system of claim 32, wherein the second mathematical expression is:

$$E(t) = Ae^{-B(t-t0))} + C$$

wherein A, B, and C are calculated using a least square fit.

38. The thermographic testing system of claim 32, wherein the computing device further comprises
- generating an attribute map from the first and second mathematical expressions, wherein the attribute map is selected from the group consisting of
  - a maximum or minimum amplitude of each time history of temperature change of the component,
  - time of occurrence of the maximum or minimum amplitude,
  - a time at which a half-maximum occurs, and
  - a derivative of the first and second mathematical expressions.

* * * * *